(12) United States Patent
Ito et al.

(10) Patent No.: US 12,037,319 B2
(45) Date of Patent: Jul. 16, 2024

(54) CURABLE COMPOUND

(71) Applicant: DAICEL CORPORATION, Osaka (JP)

(72) Inventors: Daisuke Ito, Tokyo (JP); Tsukasa Yoshida, Tokyo (JP); Toshihiro Tai, Tokyo (JP); Hitomi Tamaoki, Tokyo (JP); Satoru Sumimoto, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 791 days.

(21) Appl. No.: 17/254,053

(22) PCT Filed: Jun. 10, 2019

(86) PCT No.: PCT/JP2019/022929
§ 371 (c)(1),
(2) Date: Dec. 18, 2020

(87) PCT Pub. No.: WO2019/244694
PCT Pub. Date: Dec. 26, 2019

(65) Prior Publication Data
US 2021/0253527 A1   Aug. 19, 2021

(30) Foreign Application Priority Data
Jun. 20, 2018 (JP) ................. 2018-117283

(51) Int. Cl.
| | |
|---|---|
| *C07D 209/48* | (2006.01) |
| *C07C 225/22* | (2006.01) |
| *C07D 207/452* | (2006.01) |
| *C09D 4/00* | (2006.01) |
| *C09D 139/04* | (2006.01) |
| *C09D 149/00* | (2006.01) |
| *C09J 4/00* | (2006.01) |
| *C09J 139/04* | (2006.01) |
| *C09J 149/00* | (2006.01) |
| *C09K 3/10* | (2006.01) |

(52) U.S. Cl.
CPC .......... *C07D 209/48* (2013.01); *C07C 225/22* (2013.01); *C07D 207/452* (2013.01); *C09D 4/00* (2013.01); *C09D 139/04* (2013.01); *C09D 149/00* (2013.01); *C09J 4/00* (2013.01); *C09J 139/04* (2013.01); *C09J 149/00* (2013.01); *C09K 3/10* (2013.01); *C07C 2601/16* (2017.05); *C09K 2200/0615* (2013.01)

(58) Field of Classification Search
CPC .............. C07D 209/48; C07D 207/452; C07C 225/22; C07C 2601/16; C09D 4/00; C09D 139/04; C09D 149/00; C09J 4/00; C09J 139/04; C09J 149/00; C09K 3/10; C09K 2200/0615
USPC ....................................................... 524/850
See application file for complete search history.

(56) References Cited

U.S. PATENT DOCUMENTS

| | | | |
|---|---|---|---|
| 4,320,224 | A | 3/1982 | Rose et al. |
| 4,691,025 | A | 9/1987 | Domeier et al. |
| 6,281,323 | B1 | 8/2001 | Yokota et al. |
| 7,897,715 | B1 | 3/2011 | Laskoski et al. |
| 2013/0112460 | A1 | 5/2013 | Aoshima et al. |
| 2019/0119489 | A1 | 4/2019 | Nakatani et al. |
| 2020/0079726 | A1 | 3/2020 | Yang et al. |

FOREIGN PATENT DOCUMENTS

| | | |
|---|---|---|
| CN | 107263965 A | 10/2017 |
| JP | 60-32642 B2 | 7/1985 |
| JP | 2000-219741 A | 8/2000 |
| JP | 2000-248252 A | 9/2000 |
| JP | 2001-323067 A | 11/2001 |
| JP | 2003-213130 A | 7/2003 |
| WO | WO 2017/169738 A1 | 10/2017 |
| WO | WO 2018/107453 A1 | 6/2018 |
| WO | WO 2018/107929 A1 | 6/2018 |

OTHER PUBLICATIONS

Hedrick et al., "Elastomeric Behaviour of Crosslinked Polyaryl ether ketone)s at Elevated Temperatures," Polymer, vol. 33, No. 23, 1992, pp. 5094-5097. (Year: 1992).*

Hedrick et al., "Electromagnetic Processing of Polymers: Basic Concepts and Molecular Designs of the Macromolecules," Material Research Society Symposium Proceeding, vol. 189, 1991, pp. 421-430. (Year: 1991).*

Hedrick et al., "Microwave Processing of Functionalized Poly(arylene ether ketones)," Proceedings of the ACS Division of Polymeric Materials: Science and Engineering, Dallas Texas, USA, vol. 60, Spring Meeting, 1989, pp. 438-442. (Year: 1989).*

Hedrick et al., "Novel High Temperature Elastomers: Poly(Aryl Ether Ketones)," Polymer Preprints, vol. 31. No. 4, 1990, pp. 444-445. (Year: 1990).*

Lewis et al., "Microwave Processing of Polymers," Materials Research Society Symposium Proceedings, vol. 124, 1988. pp. 181-188. (Year: 1988).*

(Continued)

*Primary Examiner* — Ling Siu Cho
*Assistant Examiner* — Ronald Grinsted
(74) *Attorney, Agent, or Firm* — Birch, Stewart, Kolasch & Birch, LLP

(57) ABSTRACT

Provided is a curable compound having a low melting temperature, having excellent workability as a result of having good solvent solubility, and being capable of forming a cured product having excellent heat resistance. The curable compound according to an embodiment of the present invention includes the following characteristics (a) to (e). (a) Number average molecular weight (calibrated with polystyrene standard): 1000 to 15000. (b) Proportion of a structure derived from an aromatic ring in the total amount of the curable compound: 50 wt. % or greater. (c) Solvent solubility at 25° C.: 1 g/100 g or greater. (d) Glass transition temperature: 280° C. or lower. (e) 5% Weight loss temperature ($T_{d5}$) measured at a rate of temperature increase of 10° C./min (in nitrogen), for a cured product of the curable compound: 300° C. or higher.

13 Claims, 17 Drawing Sheets

(56) References Cited

OTHER PUBLICATIONS

Lyle et al., "Synthesis and Characterization of Maleimide Terminated polyarylene ether ketones," Polyimides: Materials, Chemistry and Characterization, 1989, (Proceedings of the Third International Conference on Polyimides, Ellenville, New York, Nov. 2-4, 1988, pp. 213-227. (Year: 1988).*
Lyle et al., "Synthesis, Curing and Physical Behavior of Maleimide-Terminated Poly (ether ketones)," Polymer, 1989, vol. 30, No. 6, pp. 978-985. (Year: 1989).*
Lyle et al.. Synthesis, Curing, and Physical Behavior of Maleimide Terminated Polyarylene ethers}, Polymer Preprints, vol. 29, No. 1, 1988, pp. 346-348. (Year: 1988).*
Wu et al., "Synthesis, Curing and Physical Behavior of Maleimide and Nadimide Terminated Poly(Arylene Ether Ketone) Networks." 34th international SAMPE Symposium, vol. 34, May 8-11, 1989 pp. 135-149 (Year: 1989).*
Extended European Search Report for European Application No. 19823280.3, dated Apr. 12, 2022.
Hedrick et al., "Elastomeric Behaviour of Crosslinked Poly(aryl ether ketone)s at Elevated Temperatures," Polymer, vol. 33, No. 23, 1992, pp. 5094-5097.
Hedrick et al., "Electromagnetic Processing of Polymers: I. Basic Concepts and Molecular Designs of the Macromolecules," Materials Research Society Symposium Proceeding, vol. 189, 1991, pp. 421-430.
Hedrick et al., "Microwave Processing of Functionalized Poly(arylene etherketones)." Proceedings of the ACS Division of Polymeric Materials: Science and Engineering, Dallas Texas, USA, vol. 60, Spring Meeting, 1989, pp. 438-442 (Total 6 pages).
Hedrick et al., "Novel High Temperature Elastomers: Poly(Aryl Ether Ketones)," Polymer Preprints, vol. 31, No. 1, 1990, pp. 444-445.
International Preliminary Report on Patentability and Written Opinion of the International Searching Authority, with an English translation, dated Dec. 22, 2020, for International Application No. PCT/JP2019/022923.
International Preliminary Report on Patentability and Written Opinion of the International Searching Authority, with an English translation, dated Dec. 22, 2020, for International Application No. PCT/JP2019/022929.
International Search Report, dated Aug. 27, 2019, for International Application No. PCT/JP2019/022923, with an English translation.
International Search Report, dated Sep. 10, 2019, for International Application No. PCT/JP2019/022929, with an English translation.
Lewis et al., "Microwave Processing of Polymers," Materials Research Society Symposium, Proceedings, vol. 124, 1988, pp. 181-188.
Lyle et al., "Synthesis and Characterization of Maleimide Terminated poly(arylene ether ketone)s," Polyimides: Materials, Chemistry and Characterization, 1989, (Proceedings of the Third International Conference on Polyimides, Ellenville, New York, Nov. 2-4, 1988), pp. 213-227.
Lyle et al., "Synthesis, Curing and Physical Behavior of Maleimide-Terminated Poly (ether ketones)." Polymer, 1989, vol. 30, No. 6, pp. 978-985.
Lyle et al., "Synthesis, Curing, and Physical Behavior of Maleimide Terminated Poly(arylene ethers)," Polymer Preprints, vol. 29, No. 1, 1988, pp. 346-348.
Wu et al., "Synthesis, Curing and Physical Behavior of Maleimide and Nadimide Terminated Poly(Arylene Ether Ketone) Networks," 34th International SAMPE Symposium, vol. 34, May 8-11, 1989. pp. 139-149.
Chinese Office Action and Search Report for Chinese Application No. 201980041081.0, dated Nov. 22, 2023.

* cited by examiner

CURABLE COMPOUND

TECHNICAL FIELD

The present invention relates to a curable compound and a structure containing a cured product or semi-cured product of the curable compound. The present application claims the rights of priority of JP 2018-117283 filed in Japan on Jun. 20, 2018, the content of which is incorporated herein.

BACKGROUND ART

Engineering plastics are plastics having, for example, enhanced heat resistance and mechanical properties and are very useful as materials essential for miniaturization, weight reduction, performance enhancement and reliability enhancement of various types of parts. However, the fact that an engineering plastic has a high melting temperature and a low solvent solubility and thus has poor workability has been problematic.

For example, polyimides described in Patent Document 1 and the like have excellent heat resistance and strength characteristics but are difficult to be dissolved or melted, it has been difficult to perform melt-molding for such polyimides or to use such polyimides as matrix resins for composite materials.

Polyether ether ketone (PEEK), which is also called a "super engineering plastic", is a thermoplastic resin having excellent performances for heat resistance, flame retardance, and electrical characteristics at a continuous use temperature of 260° C.; however, because the melting point thereof is 343° C., it is especially difficult to melt the plastic as well as difficult to dissolve the plastic in a solvent, and thus poor workability has been problematic (e.g., Patent Document 2).

Therefore, a curable compound having excellent workability and being capable of forming a cured product having excellent heat resistance has been demanded.

CITATION LIST

Patent Document

Patent Document 1: JP 2000-219741 A
Patent Document 2: JP 60-032642 B

SUMMARY OF INVENTION

Technical Problem

An object of the present invention is to provide a curable compound having a low melting temperature, having excellent workability due to having good solvent solubility, and being capable of forming a cured product having excellent heat resistance.

Another object of the present invention is to provide a structural body in a particulate form or planer form, the structural body containing a cured product or the semi-cured product thereof having excellent heat resistance.

Another object of the present invention is to provide a laminate having a configuration in which a cured product having excellent heat resistance or the semi-cured product thereof and a substrate are laminated.

Another object of the present invention is to provide a method for producing a laminate having a configuration in which a cured product or the semi-cured product thereof having excellent heat resistance and a substrate are laminated.

Another object of the present invention is to provide a solid material containing a cured product or the semi-cured product thereof having excellent heat resistance.

Another object of the present invention is to provide a composite material containing a cured product or the semi-cured product thereof having excellent heat resistance and a fiber.

Another object of the present invention is to provide an adhesive agent, a sealing agent, or a paint that has a low melting temperature and good solvent solubility and that can be used in an environment where excellent heat resistance is required.

Solution to Problem

As a result of diligent research, the present inventors found that the problems described above can be solved by the curable compound having the following characteristics (a) to (e). The present invention was completed based on these findings.

Specifically, an embodiment of the present invention provides a curable compound including the following characteristics (a) to (e).
(a) Number average molecular weight (calibrated with polystyrene standard): 1000 to 15000
(b) Proportion of a structure derived from an aromatic ring in a total amount of the curable compound: 50 wt. % or greater
(c) Solvent solubility at 25° C.: 1 g/100 g or greater
(d) Glass transition temperature: 280° C. or lower
(e) 5% Weight loss temperature ($T_{d5}$) measured at a rate of temperature increase of 10° C./min (in nitrogen), for a cured product of the curable compound: 300° C. or higher An embodiment of the present invention also provides the curable compound, where the curable compound is a compound represented by Formula (1) below:

[Chem. 1]

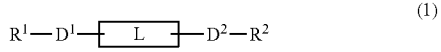

(1)

where, $R^1$ and $R^2$ are identical or different, and each represent a curable functional group, $D^1$ and $D^2$ are identical or different, and each represent a single bond or a linking group, and L represents a divalent group having a repeating unit containing a structure represented by Formula (I) below and a structure represented by Formula (II) below:

[Chem. 2]

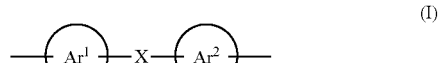

(I)

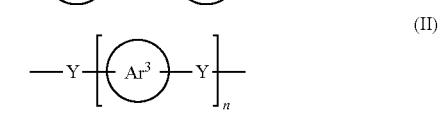

(II)

where, $Ar^1$ to $Ar^3$ are identical or different, and each represent a group in which two hydrogen atoms are removed from an aromatic ring structure or a group in which two hydrogen atoms are removed from a structure in which two or more aromatic rings are bonded through a single bond or a linking group, X represents —CO—, —S—, or —SO$_2$—, Y is identical or different, and each represents —S—, —SO$_2$—, —O—, —CO—, —COO—, or —CONH—, and n represents an integer of 0 or greater.

An embodiment of the present invention also provides the curable compound, where $R^1$ and $R^2$ in Formula (1) are identical or different, and each represent a curable functional group having a cyclic imide structure.

An embodiment of the present invention also provides the curable compound, where $R^1$ and $R^2$ in Formula (1) are identical or different, and each represent a group selected from groups represented by Formulas (r-1) to (r-6) below.

[Chem. 3]

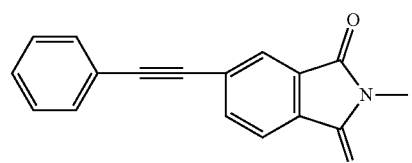
(r-1)

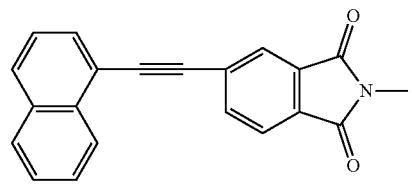
(r-2)

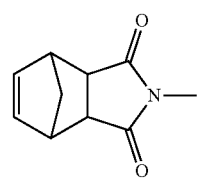
(r-3)

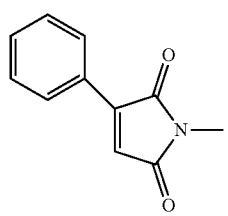
(r-4)

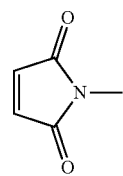
(r-5)

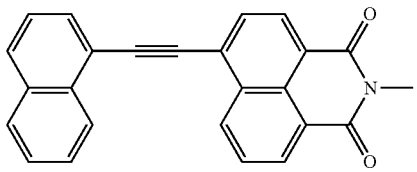
(r-6)

A bond from a nitrogen atom in the formulas bonds to $D^1$ or $D^2$.

An embodiment of the present invention also provides the curable compound, where $D^1$ and $D^2$ in Formula (1) are identical or different, and each represent a group selected from groups having structures represented by Formulas (d-1) to (d-4) below:

[Chem. 4]

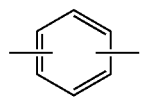
(d-1)

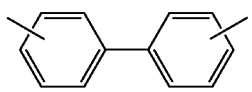
(d-2)

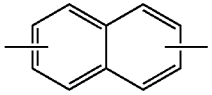
(d-3)

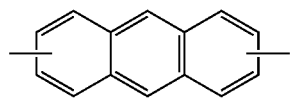
(d-4)

An embodiment of the present invention also provides the curable compound, where $Ar^1$ to $Ar^3$ in Formula (I) and Formula (II) are identical or different, and each represent a group in which two hydrogen atoms are removed from an aromatic ring structure having from 6 to 14 carbons, or a group in which two hydrogen atoms are removed from a structure in which two or more aromatic rings each having from 6 to 14 carbons are bonded through a single bond, a straight-chain or branched-chain alkylene group having from 1 to 5 carbons, or a group in which one or more hydrogen atoms of a straight-chain or branched-chain alkylene group having from 1 to 5 carbons are substituted with halogen atom(s).

An embodiment of the present invention also provides the curable compound, where the structure represented by Formula (I) is a structure derived from benzophenone.

An embodiment of the present invention also provides the curable compound, where a proportion of a structural unit derived from benzophenone in a total amount of the compound represented by Formula (1) is 5 wt. % or greater.

An embodiment of the present invention also provides the curable compound, where the structure represented by Formula (II) is a structure derived from at least one compound selected from the group consisting of hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A.

An embodiment of the present invention also provides the curable compound, where a proportion of a structural unit derived from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A in a total amount of the compound represented by Formula (1) is 5 wt. % or greater.

An embodiment of the present invention also provides a structural body in a particulate form or planer form, the structural body including a cured product or semi-cured product of the curable compound.

An embodiment of the present invention also provides a laminate having a configuration in which a cured product or semi-cured product of the curable compound and a substrate are laminated.

An embodiment of the present invention also provides a method for producing a laminate, the method including placing the curable compound on a substrate and performing heat treatment to form a laminate having a configuration in which a cured product or semi-cured product of the curable compound and the substrate are laminated.

An embodiment of the present invention also provides the method for producing a laminate, the method including coating a molten material of the curable compound on a support made of plastic, solidifying the coating, forming a thin film containing the curable compound, releasing the formed thin film from the support and laminating the formed thin film on a substrate, and performing heat treatment.

An embodiment of the present invention also provides a composite material including a cured product or semi-cured product of the curable compound and a fiber.

An embodiment of the present invention also provides a solid material including a cured product of a curable compound, where a 5% weight loss temperature ($T_{d5}$) measured at a rate of temperature increase of 10° C./min (in nitrogen) is 300° C. or higher, and a nitrogen atom content after being subjected to heat treatment at 320° C. for 30 minutes is from 2.8 to 0.1 wt. %.

An embodiment of the present invention also provides the solid material, where a peak is present in a region from 1620 to 1750 cm$^{-1}$ in an IR spectrum.

An embodiment of the present invention also provides an adhesive agent including the curable compound.

An embodiment of the present invention also provides a paint including the curable compound.

An embodiment of the present invention also provides a sealing agent including the curable compound.

Advantageous Effects of Invention

The curable compound according to an embodiment of the present invention (e.g., a compound represented by Formula (1), preferably a compound in which particular curable functional groups are introduced to both terminals of a molecular chain having a repeating unit containing a structural unit derived from benzophenone and a structural unit derived from at least one compound selected from the group consisting of hydroquinone, resorcinol, and bisphenol A) has good solvent solubility. Furthermore, the curable compound has a low melting temperature and can be melted without using a device such as an autoclave. The curable compound is thus more rapidly cured by being subjected to heat treatment or irradiation. Therefore, the curable compound according to an embodiment of the present invention has good workability (or easy moldability) and can be suitably used as, for example, an adhesive agent, a sealing agent, and a paint.

Furthermore, the curable compound according to an embodiment of the present invention can form a cured product having excellent heat resistance, flame retardance, and good dielectric properties (low relative permittivity and dielectric loss tangent). Thus, a structure that is formed from a cured product (or a semi-cured product) of the curable compound according to an embodiment of the present invention or that is at least partially containing the cured product (or the semi-cured product) can be suitably used in fields in which excellent heat resistance and good dielectric properties are required (e.g., electronic information devices, home appliances, automobiles, precision machines, aircraft, devices for the space industry).

DESCRIPTION OF EMBODIMENTS

Curable Compound

Figure 1:
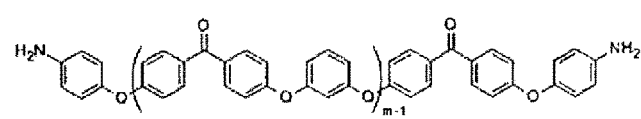
FIG. 1 is a figure showing a $^1$H-NMR spectrum (DMSO-$d_6$) of diamine (1) prepared in Preparation Example.
Figure 1:
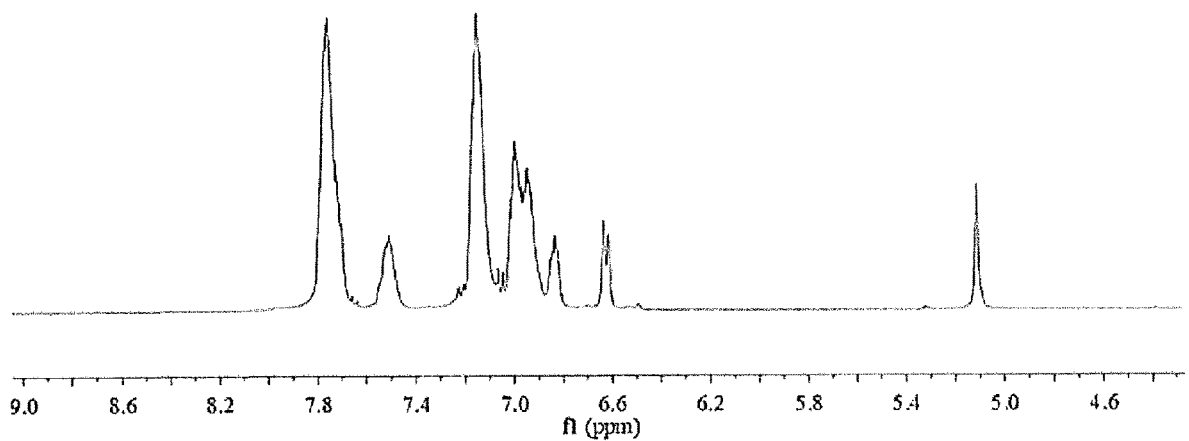
Figure 2:
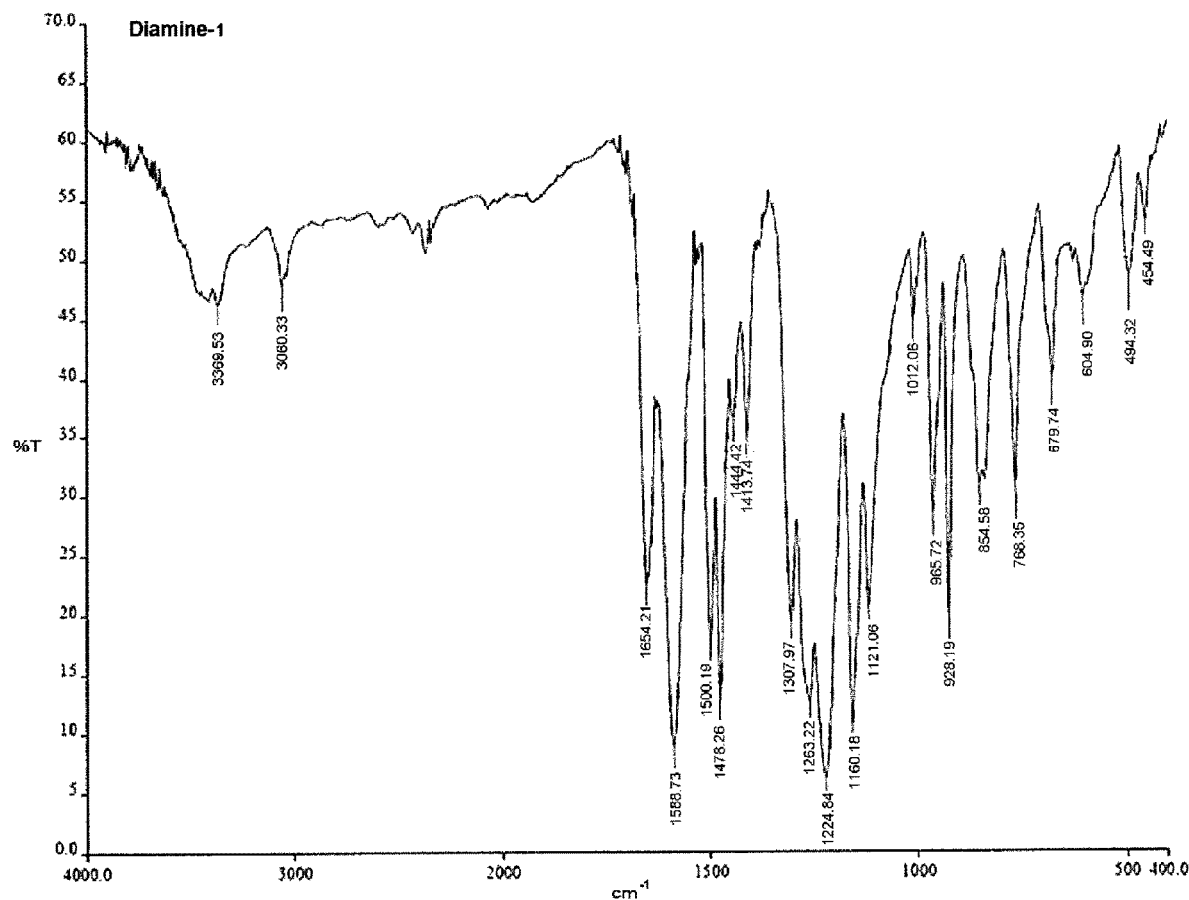
FIG. 2 is a figure showing an FTIR spectrum of diamine (1) prepared in Preparation Example.
Figure 3:
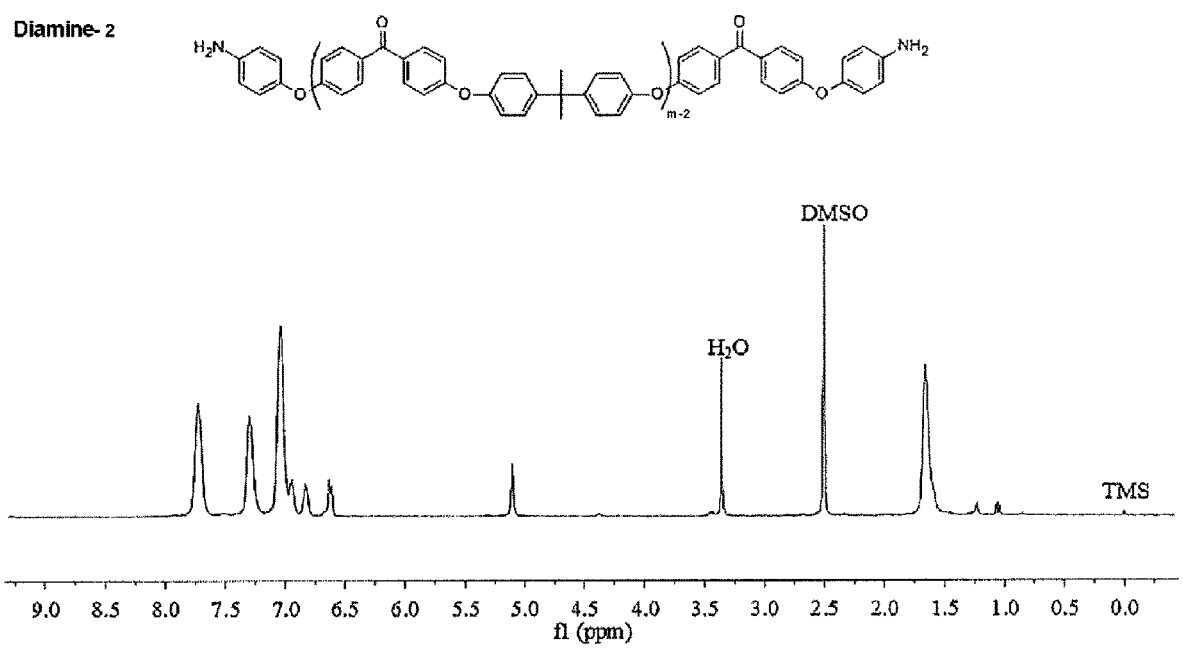
FIG. 3 is a figure showing a $^1$H-NMR spectrum (DMSO-$d_6$) of diamine (2) prepared in Preparation Example.
Figure 4:
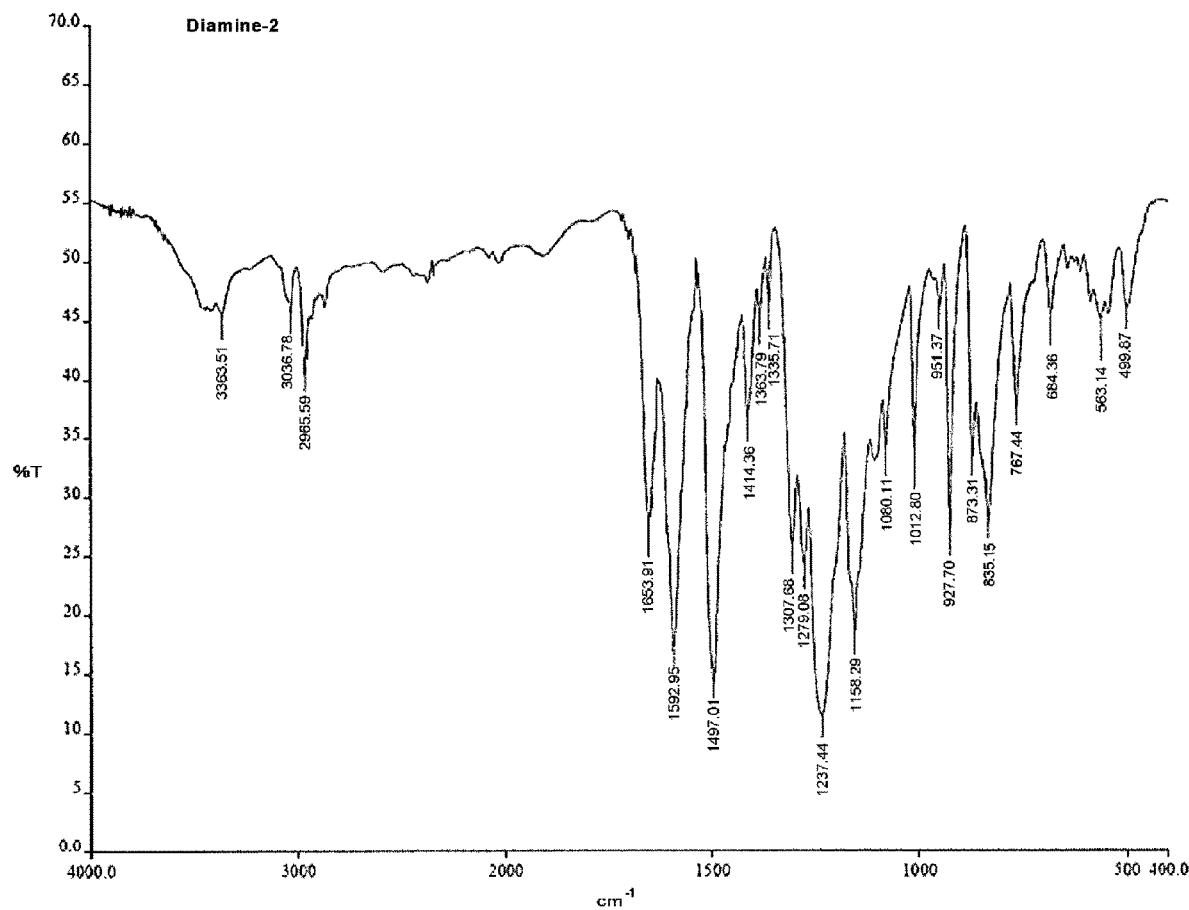
FIG. 4 is a figure showing an FTIR spectrum of diamine (2) prepared in Preparation Example.

The curable compound according to an embodiment of the present invention has the following characteristics (a) to (e).

(a) Number average molecular weight (calibrated with standard polystyrene): 1000 to 15000
(b) Proportion of a structure derived from an aromatic ring in a total amount of the curable compound: 50 wt. % or greater
(c) Solvent solubility at 25° C.: 1 g/100 g or greater
(d) Glass transition temperature: 280° C. or lower
(e) 5% Weight loss temperature ($T_{d5}$) measured at a rate of temperature increase of 10° C./min (in nitrogen), for a cured product of the curable compound: 300° C. or higher The number average molecular weight (Mn) of the curable compound is from 1000 to 15000, preferably from 1000 to 14000, particularly preferably from 1100 to 12000, and most preferably from 1200 to 10000. Therefore, while a high solubility to solvents, low melt viscosity, and easy processing are achieved, the resulting cured product (or molded body after curing) exhibits high toughness. A number average molecular weight less than the range described above tends to reduce toughness of the resulting cured product. On the other hand, a number average molecular weight greater than the range described above tends to reduce solvent solubility or increase melt viscosity excessively, thereby impairing workability. Note that Mn is determined by gel permeation chromatography (GPC) measurement (solvent: chloroform; calibrated with standard polystyrene).

The proportion of the structure derived from an aromatic ring in the total amount of the curable compound is 50 wt. % or greater and, for example, from 50 to 90 wt. %, preferably from 60 to 90 wt. %, and particularly preferably from 65 to 80 wt. %. Therefore, the curable compound has a high solvent solubility and a low melt viscosity, and the cured product thereof has a high thermal stability. A proportion of the structure derived from an aromatic ring less than the range described above tends to reduce thermal stability of the cured product. On the other hand, a proportion of the structure derived from an aromatic ring greater than the range described above tends to reduce solvent solubility, increase melt viscosity, and reduce workability.

The curable compound has good solvent solubility. Examples of the solvent include ketones, such as acetone, methyl ethyl ketone, methyl isobutyl ketone, and cyclohexanone; amides, such as formamide, acetamide, N-methyl-2-pyrrolidone (NMP), N,N-dimethylformamide, and dimethylacetamide; halogenated hydrocarbons, such as methylene chloride, chloroform, 1,2-dichloroethane, chlorobenzene, bromobenzene, dichlorobenzene, benzotrifluoride, and hexafluoro-2-propanol; sulfoxides, such as dimethylsulfoxide (DMSO), diethyl sulfoxide, and benzyl phenyl sulfoxide; ethers, such as diethyl ether, diisopropyl ether, dibutyl ether, tetrahydrofuran (THF), dioxane, 1,2-dimethoxyethane, and cyclopentyl methyl ether; esters, such as ethyl acetate; nitriles, such as acetonitrile and benzonitrile; aromatic hydrocarbons, such as benzene, toluene, and xylene; liquid mixtures of two or more types of these. The curable compound according to an embodiment of the present invention (e.g., a compound represented by Formula (1), especially, a compound represented by Formula (1), where L in the formula is a divalent group represented by Formula (1-2) or (1-3)) exhibits excellent solubility to, in particular, at least one solvent selected from the group consisting of ethers, ketones, amides, halogenated hydrocarbons, and sulfoxides (especially, at least one solvent selected from the group consisting of ethers, amides, halogenated hydrocarbons, and sulfoxides).

The solubility of the curable compound for a solvent is 1 g or greater, preferably 5 g or greater, and particularly preferably 10 g or greater, per 100 g of the solvent at 25° C.

The glass transition temperature (Tg) of the curable compound is 280° C. or lower and is, for example, from 80 to 280° C., preferably from 80 to 250° C., and particularly preferably from 100 to 200° C. Thus, the melting temperature is low, and excellent workability is achieved. When Tg is greater than the range described above, heating at a high temperature is required during melting, workability is deteriorated, and for example, in a case where a composite material is produced by impregnating fibers with the curable compound in a molten state, it may be difficult to impregnate fine fibers due to progress of a curing reaction of the curable compound. Note that Tg can be measured by a DSC method.

The nitrogen atom content of the curable compound is, for example, from 2.8 to 0.1 wt. %, preferably from 2.5 to 0.15 wt. %, more preferably from 2.0 to 0.20 wt. %, particularly preferably from 1.8 to 0.40 wt. %, and most preferably from 1.5 to 0.70 wt. %. The nitrogen atom content can be determined by, for example, CHN elemental analysis. The curable compound having the nitrogen atom content in the range described above achieves excellent solvent solubility and can form a cured product having excellent toughness and heat resistance. Meanwhile, when the nitrogen atom content is less than the range described above, formation of a cured product having excellent toughness and heat resistance tends to be difficult. Furthermore, when the nitrogen atom content is greater than the range described above, solvent solubility tends to decrease.

Furthermore, by being subjected to heat treatment, the curable compound (or curable composition described below) rapidly cures and can form a cured product having a highly crosslinked structure (that is, crosslink density is high) and having excellent heat resistance, insulation properties, and flame retardance.

The 5% weight loss temperature ($T_d5$) of a cured product of the curable compound measured at a rate of temperature increase of 10° C./min (in nitrogen) is 300° C. or higher, preferably 400° C. or higher, particularly preferably 450° C. or higher, and most preferably 500° C. or higher. The upper limit of the 5% weight loss temperature ($T_{d5}$) is, for example, 600° C., preferably 550° C., and particularly preferably 530° C. Note that the 5% weight loss temperature can be measured by thermogravimetry/differential thermal analysis (TG/DTA).

The 10% weight loss temperature ($T_{d10}$) of a cured product of the curable compound measured at a rate of temperature increase of 10° C./min (in nitrogen) is, for example, 300° C. or higher, preferably 400° C. or higher, particularly preferably 480° C. or higher, and most preferably 500° C. or higher. The upper limit of the 10% weight loss temperature ($T_{d10}$) is, for example, 600° C., and preferably 550° C. Note that the 10% weight loss temperature can be measured by thermogravimetry/differential thermal analysis (TG/DTA).

Furthermore, a cured product of the curable compound has excellent flame retardance and non-flammability of a cured product, having a thickness of 0.15 mm, measured by a method in accordance with UL94V is V-1 grade, that is, satisfies the following conditions 1 to 5.
(1) Burning duration is 30 seconds or less.
(2) Total burning duration of 5 samples is 250 seconds or less.
(3) Burning and afterglow duration after second flame application is 60 seconds or less.
(4) Combustion up to holding clamp does not occur.
(5) Burning particles do not drop and ignition of cotton batting does not occur.

A cured product of the curable compound has excellent insulation properties, and the relative permittivity thereof is, for example, 6 or less (e.g., from 1 to 6), preferably 5 or less (e.g., from 1 to 5), and particularly preferably 4 or less (e.g., from 1 to 4).

Furthermore, a cured product of the curable compound has excellent insulation properties, and the dielectric loss tangent is, for example, 0.05 or less (e.g., 0.0001 to 0.05), preferably from 0.0001 to 0.03, and particularly preferably from 0.0001 to 0.015.

Note that the "relative permittivity" and "dielectric loss tangent" described above are a value measured at a measurement frequency of 1 MHz and a measurement temperature of 23° C. in accordance with JIS-C2138 or a value measured at a frequency of 1 GHz at 23° C. in accordance with ASTM D2520.

Because the curable compound according to an embodiment of the present invention has the characteristics described above, for example, the curable compound can be used as molding materials for composite materials to be used in a severe environmental temperature, such as those for electronic information devices, home appliances, automobiles, and precision machines, and as functional materials, such as insulating materials and heat-resistant adhesive agents. Besides, the curable compound can be suitably used for sealing agents, paints, adhesive agents, inks, sealants, resists, and forming materials [forming materials for, for example, substrates, electrical insulation materials (such as electrical insulation films), laminated plates, composite materials (such as fiber-reinforced plastics and prepregs), optical elements (such as lenses), optical shaping materials, electronic papers, touch panels, solar cell substrates, optical waveguide materials, light guide plates, and holographic memories]. Furthermore, the curable compound according to an embodiment of the present invention can be suitably used for insulating materials because the cured product thereof has low relative permittivity and dielectric loss tangent.

Because the curable compound according to an embodiment of the present invention has the characteristics described above, the curable compound can be particularly suitably used as a sealing agent that covers a semiconductor element in a highly heat-resistant and highly voltage-resistant semiconductor device (such as power semiconductor), for which employment of a known resin material has been difficult.

Furthermore, because the curable compound according to an embodiment of the present invention has the characteristics described above, the curable compound can be suitably used as an adhesive agent [e.g., heat-resistant adhesive agent used for laminating a semiconductor in a highly heat-resistant and highly voltage-resistant semiconductor device (such as power semiconductor)].

Furthermore, because the curable compound according to an embodiment of the present invention has the characteristics described above, the curable compound can be suitably used as a paint (or powder coating agent) [e.g., paint (or powder coating agent) used for a highly heat-resistant and highly voltage-resistant semiconductor device (such as power semiconductor)].

Compound Represented by Formula (1)

The curable compound is a compound having a structural unit derived from an aromatic ring and a curable functional group, and the proportion of the structural unit derived from an aromatic ring in the total amount of the curable compound is 50 wt. % or greater.

The curable functional group is preferably a curable functional group having a cyclic imide structure, particularly preferably a curable functional group having an unsaturated cyclic imide structure or a curable functional group having a cyclic imide structure having an arylethynyl group, and most preferably a group selected from the groups represented by Formulas (r-1) to (r-6) below, and especially preferably a group represented by Formula (r-1) or (r-5) below.

Furthermore, the curable compound is preferably a compound represented by Formula (1) below.

[Chem. 5]

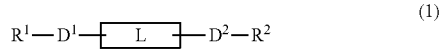

(1)

In Formula (1), $R^1$ and $R^2$ are identical or different, and each represent a curable functional group, $D^1$ and $D^2$ are identical or different, and each represent a single bond or a linking group. L represents a divalent group having a repeating unit containing a structure represented by Formula (I) below and a structure represented by Formula (II) below.

[Chem. 6]

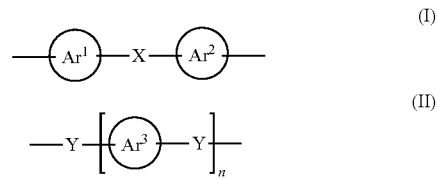

In the formula, $Ar^1$ to $Ar^3$ are identical or different, and each represent a group in which two hydrogen atoms are removed from an aromatic ring structure or a group in which two hydrogen atoms are removed from a structure in which two or more aromatic rings are bonded through a single bond or a linking group. X represents —CO—, —S—, or —SO$_2$—, Y is identical or different, and each represents —S—, —SO$_2$—, —O—, —CO—, —COO—, or —CONH—. n represents an integer of 0 or greater.

In the formula, $R^1$ and $R^2$ each represent a curable functional group. $R^1$ and $R^2$ may be identical or different. As the curable functional group of $R^1$ and $R^2$, for example, a curable functional group having a cyclic imide structure, such as a group represented by Formula (r) below, is preferred.

[Chem. 7]

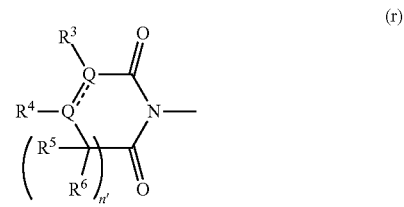

A bond from a nitrogen atom in the formulas bonds to $D^1$ or $D^2$.

In Formula (r) above, Q represents C or CH. Two Q moieties in the formula is bonded through a single bond or a double bond. n' is an integer of 0 or greater (e.g., an integer from 0 to 3, and preferably 0 or 1). $R^3$ to $R^6$ are identical or different, and each represent a hydrogen atom, a saturated or unsaturated aliphatic hydrocarbon group (preferably an alkyl group having from 1 to 10 carbons, an alkenyl group having from 2 to 10 carbons, or an alkynyl group having from 2 to 10 carbons), an aromatic hydrocarbon group (preferably an aryl group having from 6 to 10 carbons, such as a phenyl group or a naphthyl group), or a group in which two or more groups selected from the group consisting of the saturated or unsaturated aliphatic hydrocarbon groups and aromatic hydrocarbon groups described above are bonded. Two groups selected from $R^3$ to $R^6$ may be bonded each other to form a ring together with adjacent carbon atoms.

Examples of the ring that may be formed together with adjacent carbon atoms by allowing two groups selected from $R^3$ to $R^6$ to bond each other include alicyclic rings having from 3 to 20 carbons and aromatic rings having from 6 to 14 carbons. Examples of the alicyclic rings having from 3 to 20 carbons include approximately 3 to 20-membered (preferably 3 to 15-membered, particularly preferably 5 to 8-membered) cycloalkane rings, such as a cyclopropane ring, a cyclobutane ring, a cyclopentane ring, and a cyclohexane ring; approximately 3 to 20-membered (preferably 3 to 15-membered, particularly preferably 5 to 8-membered) cycloalkene rings, such as a cyclopentene ring and a cyclohexene ring; and bridged cyclic hydrocarbon groups, such as a perhydronaphthalene ring, a norbornane ring, a norbornene ring, an adamantane ring, a tricyclo[5.2.1.0$^{2,6}$]decane ring, and a tetracyclo[4.4.0.1$^{2,5}$.1$^{7,10}$]dodecane ring. The aromatic rings having from 6 to 14 carbons include a benzene ring and a naphthalene ring.

The curable functional group having a cyclic imide structure is, in particular, preferably a curable functional group having an unsaturated cyclic imide structure or a curable functional group having a cyclic imide structure having an arylethynyl group, and particularly preferably a group selected from the groups represented by Formulas (r-1) to (r-6) below, and especially preferably a group represented by Formula (r-1) or (r-5) below.

[Chem. 8]

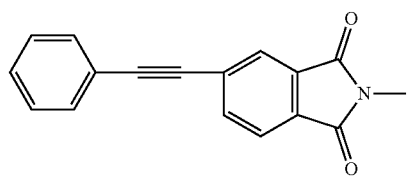
(r-1)

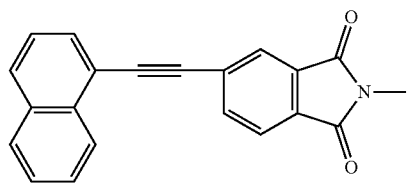
(r-2)

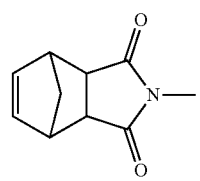
(r-3)

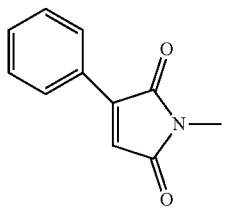
(r-4)

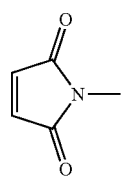
(r-5)

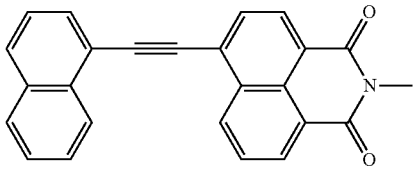
(r-6)

A bond from a nitrogen atom in the formulas bonds to $D^1$ or $D^2$ in Formula (1).

One or two or more substituents may be bonded to each of the groups represented by Formulas (r-1) to (r-6) above. Examples of the substituent include alkyl groups each having from 1 to 6 carbons, alkoxy groups each having from 1 to 6 carbons, and halogen atoms.

Examples of the alkyl group having from 1 to 6 carbons include straight-chain or branched-chain alkyl groups, such as a methyl group, an ethyl group, a propyl group, an isopropyl group, a butyl group, an isobutyl group, an s-butyl group, a t-butyl group, a pentyl group, and a hexyl group.

Examples of the alkoxy group having from 1 to 6 carbons include straight-chain or branched-chain alkoxy groups, such as a methoxy group, an ethoxy group, a butoxy group, and a t-butyloxy group.

In Formula (1), $D^1$ and $D^2$ are identical or different, and each represent a single bond or a linking group. Examples of the linking group include divalent hydrocarbon groups, divalent heterocyclic groups, a carbonyl group, an ether bond, an ester bond, a carbonate bond, an amido bond, an imido bond, and groups made by linking a plurality of these.

The divalent hydrocarbon group includes a divalent aliphatic hydrocarbon group, a divalent alicyclic hydrocarbon group, and a divalent aromatic hydrocarbon group.

Examples of the divalent aliphatic hydrocarbon group include straight-chain or branched-chain alkylene groups each having from 1 to 18 carbons and straight-chain or branched-chain alkenylene groups each having from 2 to 18 carbons. Examples of the linear or branched alkylene group having from 1 to 18 carbons include a methylene group, a methyl methylene group, a dimethyl methylene group, an ethylene group, a propylene group, and a trimethylene group. Examples of the straight-chain or branched-chain alkenylene group having from 2 to 18 carbons include a vinylene group, a 1-methylvinylene group, a propenylene group, a 1-butenylene group, and a 2-butenylene group.

The divalent alicyclic hydrocarbon group include divalent alicyclic hydrocarbon groups each having from 3 to 18 carbons, and examples thereof include cycloalkylene groups (including cycloalkylidene groups), such as a 1,2-cyclopentylene group, a 1,3-cyclopentylene group, a cyclopentylidene group, a 1,2-cyclohexylene group, a 1,3-cyclohexylene group, a 1,4-cyclohexylene group, and a cyclohexylidene group.

Examples of the divalent aromatic hydrocarbon group include arylene groups each having from 6 to 14 carbons, and examples thereof include a 1,4-phenylene group, a 1,3-phenylene group, a 4,4'-biphenylene group, a 3,3'-biphenylene group, a 2,6-naphthalenediyl group, a 2,7-naphthalenediyl group, a 1,8-naphthalenediyl group, and an anthracenediyl group.

Heterocycles constituting the divalent heterocyclic groups include aromatic heterocycles and nonaromatic heterocycles. Examples of such a heterocycle include 3 to 10-membered rings (preferably 4 to 6-membered rings) having carbon atoms and at least one heteroatom (e.g., oxygen atom, sulfur atom, or nitrogen atom) as atoms constituting the ring, and condensed rings thereof. Specific examples thereof include heterocyclic rings containing an oxygen atom as a heteroatom (e.g., 3-membered rings, such as an oxirane ring; 4-membered rings, such as an oxetane ring; 5-membered rings, such as a furan ring, a tetrahydrofuran ring, an oxazole ring, an isoxazole ring, and a y-butyrolactone ring; 6-membered rings, such as a 4-oxo-4H-pyran ring, a tetrahydropyran ring, and a morpholine ring; condensed rings, such as a benzofuran ring, an isobenzofuran ring, a 4-oxo-4H-chromene ring, a chroman ring, and an isochroman ring; crosslinked rings, such as a 3-oxatricyclo[4.3.1.1$^{4,8}$]undecan-2-one ring and a 3-oxatricyclo[4.2.1.0$^{4,8}$]nonan-2-one ring), heterocyclic rings containing a sulfur atom as a heteroatom (e.g., 5-membered rings, such as a thiophene ring, a thiazole ring, an isothiazole ring, and a thiadiazole ring; and 6-membered rings, such as a 4-oxo-4H-thiopyran ring; condensed rings, such as a benzothiophene ring), and heterocyclic rings containing a nitrogen atom as a heteroatom (e.g., 5-membered rings, such as a pyrrole ring, a pyrrolidine ring, a pyrazole ring, an imidazole ring, and a triazole ring; 6-membered rings, such as an isocyanuric ring, a pyridine ring, a pyridazine ring, a pyrimidine ring, a pyrazine ring, a piperidine ring, and a piperazine ring; condensed rings, such as an indole ring, an indoline ring, a quinoline ring, an acridine ring, a naphthyridine ring, a quinazoline ring, and a purine ring). The divalent heterocyclic group is a group in which two hydrogen atoms are removed from the heterocyclic ring structure described above.

$D^1$ and $D^2$ described above particularly preferably include a divalent aromatic hydrocarbon group, from the perspective of forming a cured product having outstanding heat resistance. The divalent aromatic hydrocarbon group is preferably a divalent aromatic hydrocarbon group having from 6 to 14 carbons, more preferably a group selected from the groups represented by Formulas (d-1) to (d-4) below, and especially preferably a group represented by Formula (d-1) below (1,2-phenylene group, 1,3-phenylene group, or 1,4-phenylene group).

[Chem. 9]

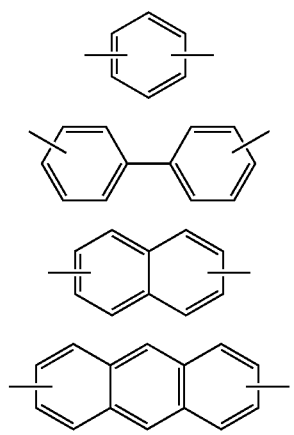

Furthermore, as $D^1$ and $D^2$ describe above, a group in which, together with the divalent aromatic hydrocarbon group, at least one group selected from the group consisting of a carbonyl group, an ether bond, an ester bond, a carbonate bond, an amido bond, and an imido bond is linked is preferred, and especially, a group in which an ether bond is linked to the divalent aromatic hydrocarbon group described above is preferred.

Thus, the $R^1$-$D^1$-moiety and the $R^2$-$D^2$-moiety in Formula (1) are identical or different, and are each preferably a group containing a group represented by Formula (rd-1) or (rd-2) below, and particularly preferably a group represented by Formula (rd-1-1) or (rd-2-1) below.

[Chem. 10]

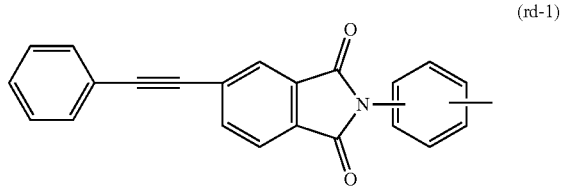

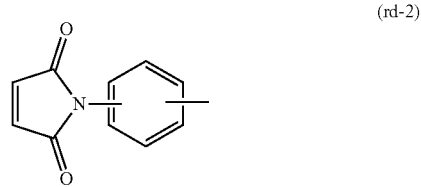

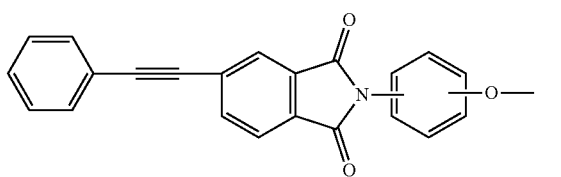

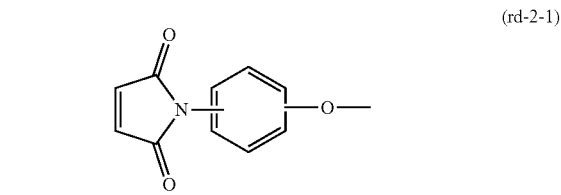

A bond from a phenylene group or an oxygen atom in the formulas bonds to L in Formula (1).

L in Formula (1) represents a divalent group having a repeating unit containing a structure represented by Formula (I) above and a structure represented by Formula (II) above. In Formula (I) and Formula (II), $Ar^1$ to $Ar^3$ are identical or different, and each represent a group in which two hydrogen atoms are removed from an aromatic ring structure or a group in which two hydrogen atoms are removed from a structure in which two or more aromatic rings are bonded through a single bond or a linking group. X represents —CO—, —S—, or —SO$_2$—, Y is identical or different, and each represents —S—, —SO$_2$—, —O—, —CO—, —COO—, or —CONH—. n represents an integer of 0 or greater and is, for example, an integer from 0 to 5, preferably an integer from 1 to 5, and particularly preferably an integer from 1 to 3.

Examples of the aromatic ring (=aromatic hydrocarbon ring) include aromatic rings having from 6 to 14 carbons, such as benzene, naphthalene, anthracene, and phenanthrene. In an embodiment of the present invention, among these, an aromatic ring having from 6 to 10 carbons, such as benzene or naphthalene, is preferred.

Examples of the linking group include divalent hydrocarbon groups having from 1 to 5 carbons and groups in which one or more hydrogen atoms of a divalent hydrocarbon group having from 1 to 5 carbons is substituted with halogen atom(s).

Examples of the divalent hydrocarbon groups having from 1 to 5 carbons include straight-chain or branched-chain alkylene groups having from 1 to 5 carbons, such as a methylene group, a methylmethylene group, a dimethylmethylene group, a dimethylene group, and a trimethylene group; straight-chain or branched-chain alkenylene groups having from 2 to 5 carbons, such as a vinylene group, 1-methylvinylene group, and a propenylene group; and straight-chain or branched-chain alkynylene groups having from 2 to 5 carbons, such as an ethynylene group, a propynylene group, and 1-methylpropynylene group. In an embodiment of the present invention, among these, a straight-chain or branched-chain alkylene group having from 1 to 5 carbons is preferred, and a branched-chain alkylene group having from 1 to 5 carbons is particularly preferred.

Thus, $Ar^1$ to $Ar^3$ described above are identical or different, and are each preferably a group in which two hydrogen atoms are removed from an aromatic ring structure having from 6 to 14 carbons, or a group in which two hydrogen atoms are removed from a structure in which two or more aromatic rings each having from 6 to 14 carbons are bonded through a single bond, a straight-chain or branched-chain alkylene group having from 1 to 5 carbons, or a group in which one or more hydrogen atoms of a straight-chain or branched-chain alkylene group having from 1 to 5 carbons are substituted with halogen atom(s), and are each particularly preferably a group in which two hydrogen atoms are removed from an aromatic ring structure having from 6 to 14 carbons, or a group in which two hydrogen atoms are removed from a structure in which two or more aromatic rings each having from 6 to 14 carbons are bonded through a single bond, a branched-chain alkylene group having from 1 to 5 carbons, or a group in which one or more hydrogen atoms of a branched-chain alkylene group having from 1 to 5 carbons are substituted with halogen atom(s).

$Ar^1$ to $Ar^3$ described above are especially preferably identical or different. and are each a group selected from the groups represented by Formulas (a-1) to (a-5) below. Note that, in the following formulas, positions of bonding are not particularly limited.

[Chem. 11]

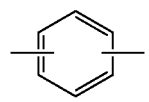
(a-1)

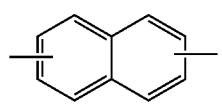
(a-2)

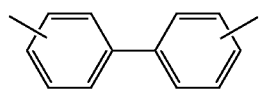
(a-3)

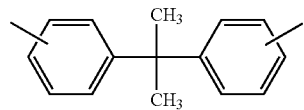
(a-4)

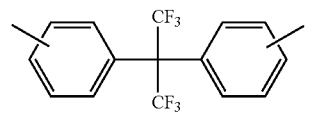
(a-5)

Among these, $Ar^1$ and $Ar^2$ in Formula (I) is preferably a group in which two hydrogen atoms are removed from an aromatic ring structure having from 6 to 14 carbons, and particularly preferably a group represented by Formula (a-1) or (a-2) above. Furthermore, among these, X is preferably —CO— or —$SO_2$—. The structure represented by Formula (I) especially preferably contains a structure derived from benzophenone.

The proportion of the structure derived from an aromatic ring in the total amount of the compound represented by Formula (1) is 50 wt. % or greater, for example, from 50 to 90 wt. %, preferably from 60 to 90 wt. %, and particularly preferably from 65 to 80 wt. %.

The proportion of the structural unit derived from benzophenone in the total amount of the compound represented by Formula (1) is, for example, 5 wt. % or greater, preferably from 10 to 62 wt. %, and particularly preferably from 15 to 60 wt. %.

$Ar^3$ in Formula (II) is, in particular, preferably a group selected from the groups represented by Formulas (a-1), (a-4), and (a-5) above. Furthermore, in particular, Y is preferably —S—, —O—, or —$SO_2$—. The structure represented by Formula (II) preferably includes a structure derived from at least one compound selected from the group consisting of hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A, and particularly preferably includes a structure derived from at least one compound selected from the group consisting of hydroquinone, resorcinol, and bisphenol A.

The proportion of a structural unit derived from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A in the total amount of the compound represented by Formula (1) is, for example, 5 wt. % or greater, preferably from 10 to 55 wt. %, and particularly preferably from 15 to 53 wt. %.

Furthermore, the proportion of the structural unit derived from hydroquinone, resorcinol, and bisphenol A in the total amount of the compound represented by Formula (1) is, for example, 5 wt. % or greater, preferably from 10 to 55 wt. %, and particularly preferably from 15 to 53 wt. %.

L in Formula (1) is, in particular, preferably a divalent group represented by Formula (L-1) below from the perspective of forming a cured product having outstanding heat resistance.

[Chem. 12]

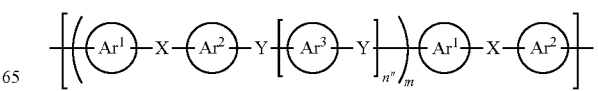
(L-1)

In Formula (L-1) above, m is a number of repeating unit shown in round brackets included in the molecular chain (=divalent group represented by Formula (L-1) above), that is, the average degree of polymerization, and is, for example, from 2 to 50, preferably from 3 to 40, more preferably from 4 to 30, particularly preferably from 5 to 20, and most preferably from 5 to 10. In the case where m is less than 2, strength and heat resistance of the resulting cured product tend to be insufficient. On the other hand, in the case where m is greater than 50, the melting temperature tends to be high. In addition, the solvent solubility tends to decrease. Note that the value of m can be determined by GPC measurement or spectrum analysis of NMR. Furthermore, n" in Formula (L-1) above represents an integer of 0 or greater, and $Ar^1$ to $Ar^3$ are identical to those described above. Note that a plurality of $Ar^1$ moieties in Formula (L-1) above represent identical groups. The same applies for $Ar^2$ and $Ar^3$.

L in Formula (1) is especially preferably a divalent group represented by Formula (L-1-1) or (L-1-2) below.

Meanwhile, when the average degree of polymerization of the molecular chain is less than the range described above, the resulting cured product tends to be brittle and mechanical characteristics tends to decrease. Furthermore, when the average degree of polymerization of the molecular chain is greater than the range described above, workability tends to decrease due to, for example, decrease of solubility to a solvent and increase of melt viscosity.

The compound represented by Formula (1) above can be produced by using, for example, a synthesis method described in Polymer p. 978 (1989). One example of a production method of the compound represented by Formula (1) above is described below; however, production of the present invention is not limited by this production method.

The compound represented by Formula (1a) below can be produced by, for example, steps [1] to [3] below. In the formula below, $Ar^1$ to $Ar^3$, X, Y, n, $R^3$ to $R^6$, Q, and n' are identical to those described above. D represents a linking group, and Z represents a halogen atom. m is the average

[Chem. 13]

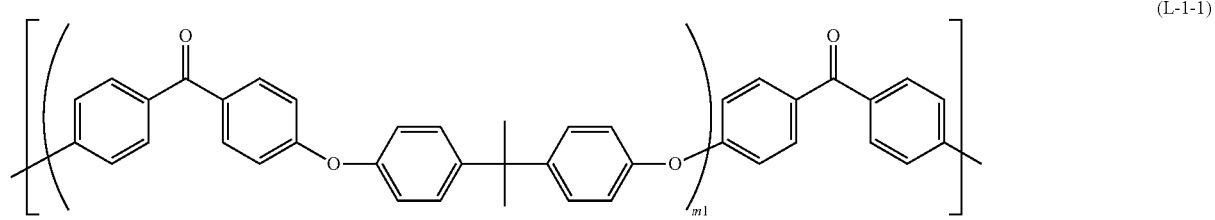

(L-1-1)

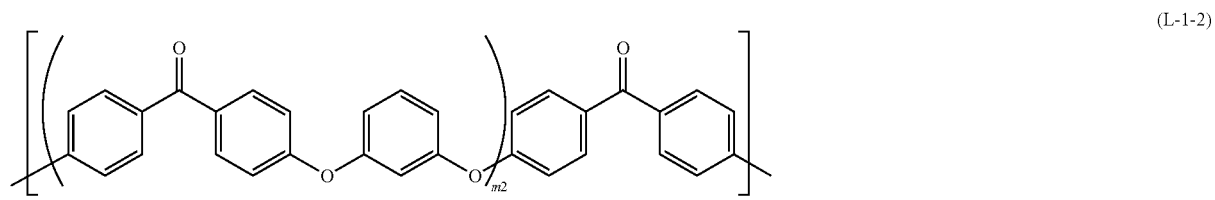

(L-1-2)

In the formula above, m1 and m2 each are a number of repeating unit shown in round brackets included in the molecular chain (=divalent group represented by Formula (L-1-1) or (L-1-2) above), that is, the average degree of polymerization, and each are, for example, from 2 to 50, preferably from 3 to 40, more preferably from 4 to 30, particularly preferably from 5 to 20, and most preferably from 5 to 10. Note that the values of m1 and m2 can be determined by GPC measurement or spectrum analysis of NMR.

Furthermore, among the compounds represented by Formula (1), a compound, in which L in Formula (1) is a divalent group represented by Formula (L-1-1) or (L-1-2) above and m1 and m2 in the formula are each from 5 to 10, can be melt-molded at a lower temperature compared to that for PEEK or the like because melting occurs at 300° C. or lower (approximately 250° C.), and achieves outstanding workability.

degree of polymerization of the repeating unit and is, for example, from 3 to 50, preferably from 4 to 30, and particularly preferably from 5 to 20. Among the compounds represented by Formula (1) above, compounds besides the compound represented by Formula (1a) below can be produced in accordance with the following method.

Step [1]: A compound represented by Formula (2) below and a compound represented by Formula (3) below as reaction base substances are allowed to react in the presence of a base, and thus a compound represented by Formula (4) below is formed.

Step [2]: An aminoalcohol (a compound represented by Formula (5) below) is allowed to react with the compound represented by Formula (4) below, and thus a diamine represented by Formula (6) below is formed.

Step [3]: A cyclic acid anhydride (a compound represented by Formula (7) below) is allowed to react with the diamine represented by Formula (6) below, and thus a compound represented by Formula (1a) below is formed.

[Chem. 14]

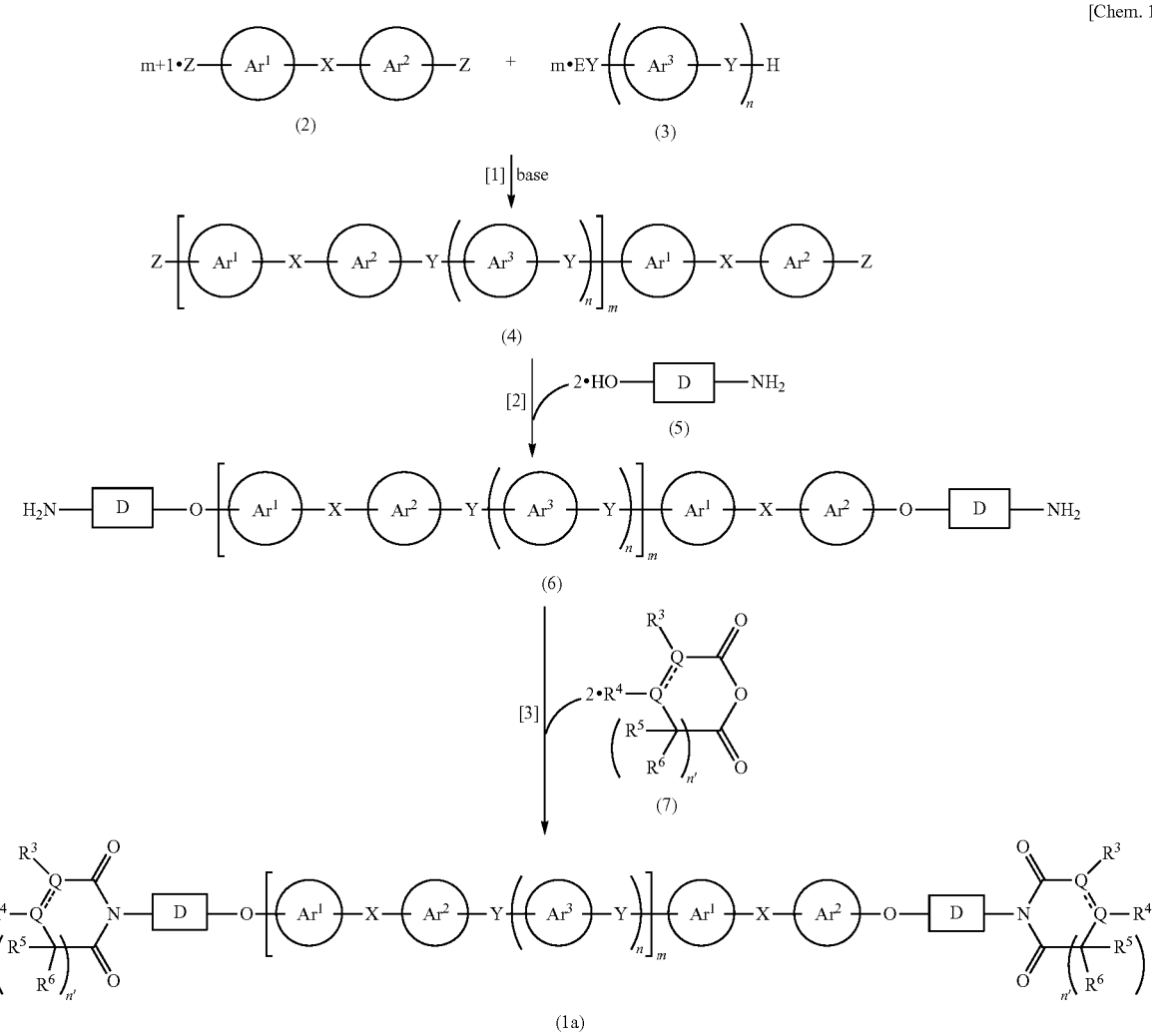

Step [1]

Examples of the compound represented by Formula (2) above include halides of benzophenone, 2-naphthyl phenyl ketone, and bis(2-naphthyl) ketone, and derivatives thereof.

Examples of the compound represented by Formula (3) above include hydroquinone, resorcinol, 2,6-naphthalenediol, 2,7-naphthalenediol, 1,5-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, bisphenol A, bisphenol F, bisphenol S, 2,5-dihydroxybiphenyl, and derivatives thereof.

Examples of the derivatives include compounds in which a substituent is bonded to an aromatic hydrocarbon group of the compound represented by Formula (2) above or the compound represented by Formula (3). Examples of the substituent include alkyl groups each having from 1 to 6 carbons, alkoxy groups each having from 1 to 6 carbons, and halogen atoms.

For the amounts of the compound represented by Formula (2) and the compound represented by Formula (3), typically, 1 mol or greater of the compound represented by Formula (2) is used relative to 1 mol of the compound represented by Formula (3), and it is desirable that the amount of the compound represented by Formula (2) be adjusted according to the average degree of polymerization of the molecular chain in a desired curable compound (1). For example, relative to 1 mol of the compound represented by Formula (3), approximately 1.2 mol (e.g., from 1.18 to 1.22 mol) of the compound represented by Formula (2) is preferably used in the case of the average degree of polymerization of 5, approximately 1.1 mol (e.g., from 1.08 to 1.12 mol) of the compound represented by Formula (2) is preferably used in the case of the average degree of polymerization of 10, and approximately 1.05 mol (e.g., from 1.04 to 1.06 mol) of the compound represented by Formula (2) is preferably used in the case of the average degree of polymerization of 20.

As the compound represented by Formula (2), at least a halide of benzophenone is preferably used, and the used amount of the halide of benzophenone is, for example, 10 mol % or greater, preferably 30 mol % or greater, particularly preferably 50 mol % or greater, and most preferably 80 mol % or greater, relative to the total used amount (100 mol %) of the compound represented by Formula (2). Note that the upper limit is 100 mol %.

As the compound represented by Formula (3), use of at least one compound selected from the group consisting of hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A (especially, at least one selected from the group consisting of hydroquinone, resorcinol, and bisphenol A) is preferred. The total of used amounts of the compounds is, for example, 10 mol % or greater, preferably 30 mol % or greater, particularly preferably 50 mol % or greater, and most preferably 80 mol % or greater, relative to the total used amount (100 mol %) of the compound represented by Formula (3). Note that the upper limit is 100 mol %.

The reaction of the compound represented by Formula (2) above and the compound represented by Formula (3) are performed in the presence of a base (e.g., at least one selected from the group consisting of inorganic bases, such as sodium hydroxide, potassium hydroxide, calcium hydroxide, sodium carbonate, potassium carbonate, and sodium hydrogencarbonate, and organic bases, such as pyridine and triethylamine). The used amount of the base can be appropriately adjusted based on the type of the base. For example, the used amount of diacidic base, such as calcium hydroxide, is approximately from 1.0 to 2.0 mol relative to 1 mol of the compound represented by Formula (3).

Furthermore, this reaction can be performed in the presence of a solvent. As the solvent, for example, an organic solvent, such as N-methyl-2-pyrrolidone, dimethylformamide, dimethyl sulfoxide, acetone, tetrahydrofuran, or toluene, or a mixed solvent of two or more thereof can be used.

The used amount of the solvent is, for example, approximately from 5 to 20 times in weight relative to the total amount (weight) of the reaction base substances. The solvent, when used in an amount greater than the range described above, decreases the concentration of the reaction base substances and tends to decrease the reaction rate.

The reaction atmosphere of the reaction above is not particularly limited as long as it does not inhibit the reaction. For example, any of an air atmosphere, a nitrogen atmosphere, and an argon atmosphere may be used.

The reaction temperature is, for example, approximately from 100 to 200° C. The reaction time is, for example, approximately from 5 to 24 hours. In addition, this reaction can be performed by any method, such as a batch method, a semi-batch method, and a continuous method.

After the completion of the reaction, the resulting reaction product can be separated and purified by a separation method, such as filtration, concentration, distillation, extraction, crystallization, adsorption, recrystallization, and column chromatography; and a separation method in combination thereof.

Step [2]

Examples of the compound represented by Formula (5) above include 4-aminophenol, 2-amino-6-hydroxynaphthalene, and regioisomers and derivatives thereof.

The used amount of the compound represented by Formula (5) above can be appropriately adjusted based on the average degree of polymerization of the molecular chain in a desired curable compound. For example, the amount may be adjusted to a range approximately from 0.4 to 0.6 mol relative to 1 mol of the compound represented by Formula (3) in the case of the average degree of polymerization of 5, approximately from 0.2 to 0.4 mol relative to 1 mol of the compound represented by Formula (3) in the case of the average degree of polymerization of 10, and approximately from 0.1 to 0.15 mol relative to 1 mol of the compound represented by Formula (3) in the case of the average degree of polymerization of 20.

Since a hydrogen halide is formed in the reaction as the reaction progresses, carrying out the reaction in the presence of a base to trap the formed hydrogen halide is preferred in that the progress of the reaction can be effectively promoted. Examples of the base include inorganic bases, such as sodium hydroxide, potassium hydroxide, calcium hydroxide, sodium carbonate, potassium carbonate, and sodium hydrogencarbonate, and organic bases, such as pyridine and triethylamine. One of these solvents can be used alone or two or more in combination.

The used amount of the base can be appropriately adjusted based on the type of the base. For example, the used amount of monoacidic base, such as sodium hydroxide, is approximately from 1.0 to 3.0 mol relative to 1 mol of the compound represented by Formula (5) above.

Furthermore, this reaction can be performed in the presence of a solvent. As the solvent, the same solvent used in Step [1] can be used.

The reaction temperature is, for example, approximately from 100 to 200° C. The reaction time is, for example, approximately from 1 to 15 hours. In addition, this reaction can be performed by any method, such as a batch method, a semi-batch method, and a continuous method.

After the completion of the reaction, the resulting reaction product can be separated and purified by a separation method, such as filtration, concentration, distillation, extraction, crystallization, adsorption, recrystallization, and column chromatography; and a separation method in combination thereof.

Step [3]

Examples of the cyclic acid anhydride (the compound represented by Formula (7) above) include maleic anhydride, 2-phenylmaleic anhydride, 4-phenylethynyl-phthalic anhydride, 4-(1-naphthylethynyl)-phthalic anhydride, and bicyclo[2.2.1]hept-5-ene-2,3-dicarboxylic anhydride, and derivatives thereof.

The used amount of the cyclic acid anhydride can be appropriately adjusted based on the average degree of polymerization of the molecular chain in a desired curable compound. For example, the amount may be adjusted to a range approximately from 0.4 to 0.8 mol relative to 1 mol of the compound represented by Formula (3) in the case of the average degree of polymerization of 5, approximately from 0.2 to 0.4 mol relative to 1 mol of the compound represented by Formula (3) in the case of the average degree of polymerization of 10, and approximately from 0.1 to 0.15 mol relative to 1 mol of the compound represented by Formula (3) in the case of the average degree of polymerization of 20.

This reaction can be performed in the presence of a solvent. As the solvent, the same solvent used in Step [1] can be used.

This reaction is preferably performed at room temperature (1 to 30° C.). The reaction time is, for example, approximately from 1 to 30 hours. In addition, this reaction can be performed by any method, such as a batch method, a semi-batch method, and a continuous method.

Furthermore, in this reaction, removal of water, formed as a by-product, by azeotropy using an azeotropic solvent of water (e.g., toluene) or by use of a dehydrating agent (e.g., acetic anhydride) is preferred from the perspective of promotion of the reaction progress. Furthermore, removal of formed water by a dehydrating agent is preferably performed in the presence of a basic catalyst (e.g., triethylamine).

After the completion of the reaction, the resulting reaction product can be separated and purified by a separation method, such as filtration, concentration, distillation, extraction, crystallization, adsorption, recrystallization, and column chromatography; and a separation method in combination thereof.

The exothermic peak temperature of the compound represented by Formula (1) depends on the type of the curable functional group but is, for example, from 170 to 450° C., preferably from 200 to 430° C., and particularly preferably from 220 to 420° C. The exothermic peak temperature is determined by DSC measurement.

Because the exothermic peak temperature of the compound represented by Formula (1) depends on the type of the curable functional group, a curable functional group is preferably selected depending on a molding method to be employed. For example, in the case where the curable compound is molded in a film form by a cast method from a solution in which the curable compound is dissolved in a solvent, and cured, a group represented by Formula (r-5) above is preferably selected as the curable functional group in the compound represented by Formula (1). In this case, a cured product can be formed by heating at a temperature of approximately 250° C. Meanwhile, when a group represented by Formula (r-1) above is selected as the curable functional group in the compound represented by Formula (1), the curable compound can be melted and molded at a temperature of approximately 300° C. or lower, and a cured product can be formed by heating at a temperature of approximately 380° C.

Note that heating may be performed while the temperature is held constant or may be performed by changing the temperature stepwise. The heating temperature can be appropriately adjusted depending on the heating time and, for example, in the case where shortening of the heating time is desired, the heating temperature is preferably set high. Because the compound represented by Formula (1) has a high proportion of the structure derived from an aromatic ring, a cured product (in detail, a cured product having excellent heat resistance) can be formed without causing decomposition even when heating is performed at a high temperature, and a cured product can be efficiently formed with superior workability by heating at a higher temperature and in a shorter period of time. Furthermore, the heating means is not particularly limited, and a known means can be used.

Curing of the compound represented by Formula (1) can be performed under normal pressure, under reduced pressure, or under pressurization.

The heating temperature and heating time of the compound represented by Formula (1) may be adjusted and curing reaction may be stopped in the middle of the reaction without completing the reaction. Thus, a semi-cured product (B-stage) can be formed. The degree of cure of the semi-cured product is, for example, 85% or less (e.g., from 10 to 85%, particularly preferably from 15 to 75%, and even more preferably from 20 to 70%).

Note that the degree of cure of the semi-cured product can be calculated from the following equation by measuring the calorific value of the compound represented by Formula (1) and the calorific value of the semi-cured product thereof by DSC. Degree of cure (%)=[1−(Calorific value of semi-cured product/Calorific value of compound represented by Formula (1))]×100

The semi-cured product of the compound represented by Formula (1) temporarily exhibits fluidity by heating and can conform to a step having a height difference. Furthermore, by performing heat treatment, a cured product having excellent heat resistance can be formed.

Curable Composition

The curable composition according to an embodiment of the present invention contains one type or two or more types of curable compounds. The content of the curable compound (in the case where two or more types are contained, the total amount thereof) in the total amount of the curable composition according to an embodiment of the present invention (or the total amount of non-volatile contents of the curable composition according to an embodiment of the present invention) is, for example, 30 wt. % or greater, preferably 50 wt. % or greater, particularly preferably 70 wt. % or greater, and most preferably 90 wt. % or greater. Note that the upper limit is 100 wt. %. That is, the curable composition according to an embodiment of the present invention may be formed from the curable compound alone.

The curable composition according to an embodiment of the present invention may contain another component as necessary in addition to the curable compound. As such another component, a known additive can be used, and examples thereof include curable compounds other than the compound represented by Formula (1) above, catalysts, fillers, organic resins (such as silicone resins, epoxy resins, and fluororesins), solvents, stabilizers (such as antioxidants, ultraviolet absorbers, light-resistant stabilizers, and heat stabilizers), flame retardants (such as phosphorus-based flame retardants, halogen-based flame retardants, and inorganic flame retardants), flame retardant aids, reinforcing materials, nucleating agents, coupling agents, lubricants, waxes, plasticizers, release agents, impact resistance modifiers, hue modifiers, fluidity improvers, colorants (such as dyes and pigments), dispersants, anti-foaming agents, defoaming agents, antibacterial agents, preservatives, viscosity modifiers, and thickening agents. One type alone or two or more types thereof in combination can be used.

The filler include organic fillers and inorganic fillers. Examples of a raw material of the filler include carbon materials (such as carbon black, artificial graphite, expandable graphite, natural graphite, coke, carbon nanotubes, and diamond), carbon compounds (such as silicon carbide, fluorine carbide, boron carbide, tungsten carbide, and titanium carbide), nitrogen compounds (such as boron nitride, aluminum nitride, titanium nitride, carbon nitride, and silicon nitride), minerals or ceramics (such as talc, mica, zeolite, ferrite, tourmaline, diatomaceous earth, fired diatomaceous earth, kaolin, sericite, bentonite, smectite, clay, silica, quartz powder, glass beads, glass powder, glass flake, milled fiber, and wollastonite), single metal or alloy (such as metal silicon, iron, copper, magnesium, aluminum, gold, silver, platinum, zinc, manganese, and stainless steel), metal oxides (such as silica, alumina, zirconia, magnesia, zinc oxide, and beryllium oxide), metal hydroxides (such as aluminum hydroxide, calcium hydroxide, and magnesium hydroxide), and carbonates (such as magnesium carbonate and calcium carbonate).

The content of the filler is in a range of, for example, 0.1 to 95 parts by weight per 100 parts by weight of the curable compound and can be appropriately adjusted based on the use.

The curable composition according to an embodiment of the present invention preferably contains at least the compound represented by Formula (1) above as the curable compound. Furthermore, the curable composition may include a curable compound besides the compound represented by Formula (1) above; however, the proportion of the compound represented by Formula (1) above in the total amount (100 wt. %) of curable compounds in the curable composition is, for example, 70 wt. % or greater, preferably 80 wt. % or greater, and particularly preferably 90 wt. % or greater. Note that the upper limit is 100 wt. %.

Since the curable composition according to an embodiment of the present invention contains the curable compound having excellent solvent solubility, the curable compound may be a solvent-dissolved material, in which the curable compound is dissolved in a solvent. As the solvent, a solvent exhibiting good solubility to the curable compound is preferred and, for example, ketones, amides, halogenated hydrocarbons, sulfoxides, ethers, esters, nitriles, aromatic hydrocarbons, and liquid mixtures of two or more of these are preferred, at least one solvent selected from the group consisting of ethers, ketones, amides, halogenated hydrocarbons, and sulfoxides is particularly preferred, and at least one solvent selected from the group consisting of ethers, amides, halogenated hydrocarbons, and sulfoxides is especially preferred.

Furthermore, even when the curable composition according to an embodiment of the present invention does not contain any crosslinking agent or curing accelerator (e.g., the total content of the crosslinking agent and the curing accelerator in the total amount of the curable composition according to an embodiment of the present invention is 3 wt. % or less, and preferably less than 1 wt. %), a cured product can be rapidly formed. Therefore, the resulting cured product has excellent heat resistance. Furthermore, because the content of an unreacted curing accelerator and decomposition products of the curing accelerator in the cured product can be suppressed to an extremely low level, outgassing originated from these can be suppressed.

Because the curable composition according to an embodiment of the present invention contains the curable compound, the curable composition rapidly cures by being heat-treated and can form a cured product having excellent heat resistance. Note that the heat treatment conditions can be appropriately set in the same range as that for the curing conditions of the curable compound described above.

Furthermore, because the curable composition according to an embodiment of the present invention contains the curable compound, the curable composition may be coated on a substrate and cured rapidly by heat treatment and thus a cured product having excellent adhesion to the substrate can be formed. The tensile shear strength (in accordance with JIS K 6850 (1999)) between the substrate and the cured product is, for example, 1 MPa or greater, preferably 5 MPa or greater, and particularly preferably 10 MPa or greater. Note that the tensile shear strength can be measured by a tensile tester (Orientec Corporation, TENSILON UCT-5T) at a pulling speed of 300 mm/min and a peeling angle of 180°.

The curable composition according to an embodiment of the present invention can be suitably used as molding materials for composite materials (such as fiber-reinforced plastics and prepregs) to be used in a severe environmental temperature, such as those for electronic information devices, home appliances, automobiles, precision machines, aircraft, devices for the space industry, and energy field (oil drill pipes/tubes and fuel containers), and as functional materials, such as shielding materials, conducting materials (such as thermally conducting materials), insulating materials, and adhesive agents (such as heat-resistant adhesive agents). In addition, the curable composition can be suitably used as sealing agents, paints, inks, sealants, resists, shaping materials, and forming materials [forming materials for, for example, automobile components, such as thrust washers, oil filters, seals, bearings, gears, cylinder head covers, bearing retainers, intake manifolds, and pedals; components of semiconductor and liquid crystal producing apparatuses, such as base materials, electrical insulation materials (such as electrical insulation films), laminated plates, electronic papers, touch panels, solar cell substrates, optical waveguide materials, light guide plates, holographic memories, silicon wafer carriers, IC chip trays, electrolytic capacitor trays, and insulating films; optical components, such as lenses; compressor components, such as pumps, valves, and seals; cabin interior components of aircraft; medical device components and components of food and beverage producing facilities, such as sterilized devices, columns, and piping; and members for electric and electronic devices as represented by housings to be used for personal computers and cell phones, and keyboard supporters being members to support keyboards inside personal computers].

Because the curable composition according to an embodiment of the present invention has the characteristics described above, especially, the curable composition can be suitably used as a sealing agent that covers a semiconductor element in a highly heat-resistant and highly voltage-resistant semiconductor device (such as power semiconductor), for which employment of a known resin material has been difficult.

Furthermore, because the curable composition according to an embodiment of the present invention has the characteristics described above, the curable composition can be suitably used as an adhesive agent [e.g., heat-resistant adhesive agent used for laminating a semiconductor in a highly heat-resistant and highly voltage-resistant semiconductor device (such as power semiconductor)].

Furthermore, because the curable composition according to an embodiment of the present invention has the characteristics described above, the curable composition can be suitably used as a paint (or powder coating agent) [e.g., paint (or powder coating agent) used for a highly heat-resistant and highly voltage-resistant semiconductor device (such as power semiconductor)].

Solid Material

The solid material according to an embodiment of the present invention contains a cured product of the curable compound and has the following properties.

Solid Material Properties:

The 5% weight loss temperature ($T_{d5}$) measured at a rate of temperature increase of 10° C./min (in nitrogen) is 300° C. or higher, and a nitrogen atom content after being subjected to heat treatment at 320° C. for 30 minutes is from 2.8 to 0.1 wt. %.

Note that the cured product of the curable compound is a crosslinked structure (or a polymer) of the curable compound.

The solid material according to an embodiment of the present invention may contain another component besides the cured product of the curable compound; however, the proportion of the cured product in the total solid content is, for example 70 wt. % or greater, preferably 80 wt. % or greater, and particularly preferably 90 wt. % or greater. Note that the upper limit is 100 wt. %.

The 5% weight loss temperature ($T_{d5}$) of the solid material is preferably 400° C. or higher, particularly preferably 450° C. or higher, and most preferably 500° C. or higher. The upper limit of the 5% weight loss temperature ($T_{d5}$) is, for example, 600° C., preferably 550° C., and particularly preferably 530° C.

Furthermore, the nitrogen atom content of the solid material after the heat treatment is, for example, from 2.8 to 0.1 wt. %, preferably from 2.5 to 0.15 wt. %, more preferably from 2.0 to 0.20 wt. %, particularly preferably from 1.8 to 0.40 wt. %, and most preferably from 1.5 to 0.70 wt. %. Therefore, the solid material according to an embodiment of the present invention has excellent toughness and heat resistance. On the other hand, when the nitrogen atom content is less than the range described above, the toughness and heat resistance of the solid material tend to decrease.

The nitrogen atom content in the solid material after the heat treatment can be determined by, for example, CHN elemental analysis.

The solid material may include other additives besides the cured product of the curable compound; however, when the solid material is subjected to heat treatment at 320° C. for 30 minutes, additives having decomposition points or boiling points of lower than 320° C. are decomposed and disappear, and thus only the cured product of the curable compound remains. Therefore, the nitrogen atom content in the cured product after the heat treatment can be estimated as the nitrogen atom content contained in the cured product of the curable compound. Note that, from the perspective of thermal history, heat treatment can be employed as the curing treatment.

Furthermore, the solid material according to an embodiment of the present invention has a peak in a region of 1620 to 1750 cm-1 of an IR spectrum. The peak is originated from the "—C(=O)—N—C(=O)—" unit.

The solid material according to an embodiment of the present invention can be produced by, for example, heat-treating a curable compound represented by Formula (1), in which $R^1$ and $R^2$ in the formula are identical or different, and are each a curable functional group having a cyclic imide structure (particularly preferably, a curable compound represented by Formula (1) above, in which $R^1$ and $R^2$ in the formula are identical or different, and are each a group selected from the groups represented by Formulas (r-1) to (r-6)) or a curable composition containing the curable compound.

Thus, the solid material according to an embodiment of the present invention preferably contains a cured product of the curable compound represented by Formula (1), in which $R^1$ and $R^2$ in the formula are identical or different, and are each a curable functional group having a cyclic imide structure (particularly preferably, a curable compound represented by Formula (1) above, in which $R^1$ and $R^2$ in the formula are identical or different, and are each a group selected from the groups represented by Formulas (r-1) to (r-6)), and the content of the cured product is, for example, 70 wt. % or greater, preferably 80 wt. % or greater, and particularly preferably 90 wt. % or greater, relative to the total amount of the solid material. Note that the upper limit is 100 wt. %.

Structural Body

The structural body according to an embodiment of the present invention is a structural body in a particulate form or planer form, the structural body containing a cured product or semi-cured product of the curable compound. The structural body according to an embodiment of the present invention can be produced by subjecting the curable compound (or the curable composition) to a molding method, such as injection molding, transfer molding, compression molding, or extrusion molding.

The structural body according to an embodiment of the present invention has excellent heat resistance and flame retardance. Furthermore, the relative permittivity and dielectric loss tangent are low. Therefore, the structural body can be suitably used as a material that can be replaced with a metal, such as iron and aluminum, in the fields of housing and building, sporting goods, automobiles, and aircraft and space industry. Furthermore, the structural body can be suitably used as a structural body to be provided at a place where flame retardance is required by the Fire Service Act, such as high-rise buildings, underground, theaters, and vehicles. In particular, a structural body in a planer form can be suitably used as an interlayer insulating film of an electric device.

Laminate

The laminate according to an embodiment of the present invention has a structure having a cured product or semi-cured product of the curable compound being laminated with a substrate. The laminate according to an embodiment of the present invention includes structures that are a cured product or semi-cured product of the curable compound/substrate and a substrate/cured product or semi-cured product of the curable compound/substrate.

Examples of the materials of the substrate include semi-conductor materials (such as ceramics, SiC, and gallium nitride), paper, coated paper, plastic films, wood, fabric, nonwoven fabric, and metals (such as stainless steel, aluminum alloy, and copper).

The laminate according to an embodiment of the present invention has a configuration in which the substrates are laminated via an adhesive layer containing a cured product or semi-cured product of the curable compound and having excellent heat resistance, flame retardance, insulation properties, and adhesion to the substrate. The laminate according to an embodiment of the present invention can be suitably used as, for example, an electric circuit substrate.

[Method for Producing Laminate]

The laminate according to an embodiment of the present invention can be produced by, for example, placing the curable compound on a substrate and performing heat treatment.

The method for producing a laminate according to an embodiment of the present invention include the following methods.

1. A method in which the curable compound is placed on a substrate as a solid (e.g., powder-like solid) and then heat treatment is performed.
2. A method in which a thin film containing the curable compound is formed on a substrate and then heat treatment is performed.
3. A method in which a thin film containing the curable compound is laminated on a substrate and then heat treatment is performed.

The heat treatment conditions can be appropriately set in the same range as those for the curing conditions of the curable compound described above.

The thin film of the method 2 described above can be produced by, for example, coating a molten material of the curable compound on a substrate and cooling the coated film.

Furthermore, the thin film can also be produced by applying a solvent-dissolved material or solvent-dispersed material of the curable compound on a substrate and drying the coated film.

In the method 3 described above, as the thin film to be laminated on the substrate, for example, a material formed by coating a molten material of the curable compound on a support, cooling the produced coated film, and then releasing the coated film from the support can be used.

Furthermore, as the thin film, a material formed by applying a solvent-dissolved material or solvent-dispersed material of the curable compound on a support, drying the produced coated film, and then releasing the coated film from the support can be also used.

To easily peel the thin film formed on the support from the support, it is required to use, as the forming material of the support, a material that does not melt at a temperature at which the thin film containing the curable compound is formed. For example, in the case where PEEK is used as the curable compound, because the PEEK is less likely to be dissolved in a solvent, a thin film needs to be formed by applying a molten material of the PEEK on a substrate; however, the melting point of the PEEK is 343° C., which is a significantly high temperature. Therefore, it is difficult to use a support made of a plastic and a support formed from, for example, a metal or glass has been used. However, the curable compound described above exhibits excellent solvent solubility at room temperature (1 to 30° C.). Furthermore, the curable compound melts at a temperature that does not melt a plastic, such as a polyimide and fluororesin. For example, in the case of the curable compound in which $R^1$ and $R^2$ in Formula (1) are each the group represented by Formula (r-5), the curing temperature is approximately 250° C. Thus, a support made of a plastic (e.g., a support formed from a polyimide or fluororesin) can be used. For example, such a support may be used as a plastic belt of a belt conveyor, and the laminate can be continuously produced on a production line including the belt conveyor.

Furthermore, the curable compound has a small cure shrinkage and excellent shape stability. Therefore, by uniformly applying the curable compound on a support or the like, a thin film having a smooth surface can be formed, and by curing this thin film, a cured product or semi-cured product having excellent surface smoothness can be formed. Therefore, the cured product or semi-cured product suitably adheres to a surface of a substrate having low flexibility or low shape conformity and thus can firmly adheres to the substrate.

The laminate can be suitably used as, for example, an electric circuit substrate.

Composite Material

The composite material according to an embodiment of the present invention has a cured product or semi-cured product of the curable compound and a fiber. The shape of the composite material is not particularly limited, and examples thereof include a fiber form and a sheet form.

Examples of the fiber include carbon fibers, aramid fibers, and glass fibers. One of these solvents can be used alone or two or more in combination. The fiber may be processed into a thread form or a sheet form (woven fabric or nonwoven fabric).

The composite material according to an embodiment of the present invention can be produced by, for example, impregnating fibers with a solution prepared by dissolving the curable compound in a solvent or impregnating fibers with a molten material of the curable compound and performing heat treatment. The heat treatment can cure or semi-cure the impregnated curable compound. The composite material formed by semi-curing the impregnated curable compound can be suitably used as an intermediate product, such as a prepreg.

The composite material according to an embodiment of the present invention has a configuration, in which the curable compound is incorporated into gaps between fibers and cured therein, and has a light weight and high strength as well as excellent heat resistance, flame retardance, and insulation properties. Therefore, the composite material can be suitably used as a material that can be replaced with a metal, such as iron and aluminum, in the fields of housing and building, sporting goods, automobiles, and aircraft and space industry. In addition, for example, the composite material can be suitably used as clothing material for fire fighting (fire fighting clothing, clothing for activity, clothing for rescue and heat resistant clothing); curtains and floor covering materials to be provided at a place where flame retardance is required by the Fire Service Act, such as high-rise buildings, underground, theaters, and vehicles; separators, such as separators for secondary batteries and separators for fuel cells; filters, such as industrial filters, filters for cars, and medical filters; and space materials.

WORKING EXAMPLE

Hereinafter, the present invention will be described more specifically with reference to examples, but the present invention is not limited by these examples.

Note that the measurements were performed under the following conditions.

NMR Measurement

Measurement instrument: BRUKER 400 MHz/54 mm or BRUKER AVANCE 600 MHz

Measurement solvent: deuterated DMSO, deuterated chloroform or a liquid mixture of deuterated chloroform/pentafluorophenol (PFP)=2/1 (wt/wt)

Chemical shift: TMS as the reference

GPC measurement

Apparatus: pump "LC-20AD" (available from Shimadzu Corporation)

Detector: RID-10A (available from Shimadzu Corporation.) or TDA-301 and UV 2501 (available from Viscotek Corporation)

Solvent: THF or chloroform

Column: Shodex GPC K-806L×one column+Shodex GPC K-803×one column+Shodex GPC K-801×2 columns Flow rate: 1.0 mL/min Temperature: 40° C.

Sample concentration: 0.1% (wt/vol)

calibrated with standard polystyrene

DSC measurement

Instrument: TA Q20

Rate of temperature increase: 10° C./min

Atmosphere: nitrogen atmosphere

TG/DTA measurement

Instrument: NETZSCH TG209 F3

Rate of temperature increase: 10° C./min

Atmosphere: nitrogen atmosphere

IR measurement

Instrument: Perkin Elmer Spectrum RX1 (ATR method)

For comparative examples, PEEK (commercially available PEEK powder, polyether ether ketone, VICTREX 151G, melting point: 343° C., Tg: 147° C.) was used.

Preparation Example 1 (Production of Diamine (1))

In a 500 mL (three-necked) flask equipped with an agitation apparatus, a nitrogen introducing tube, and Dean-Stark apparatus, 27.50 g of 4,4'-difluorobenzophenone, 11.56 g of resorcinol, 21.77 g of anhydrous potassium carbonate, 154 mL of N-methyl-2-pyrrolidone, and 77 mL of toluene were charged and heated while agitated in a nitrogen atmosphere, and the toluene was refluxed at 130 to 140° C. for 4 hours. Thereafter, further heating was performed to distill off the toluene at 170 to 180° C. Furthermore, after the agitation was continued for 10 hours at 170 to 180° C., the temperature was lowered to room temperature.

In the flask containing the product, 5.04 g of 4-aminophenol, 6.39 g of anhydrous potassium carbonate, 20 mL of N-methyl-2-pyrrolidone, and 100 mL of toluene were added.

The mixture was heated again while agitated in a nitrogen atmosphere, and the toluene was refluxed at 130 to 140° C. for 3 hours. Thereafter, heating was performed to distill off the toluene at 170 to 180° C., and agitation was continued for 4 hours while the temperature of 170 to 180° C. was further maintained. The mixture was then cooled to room temperature, and the reaction solution was added to 3000 mL of methanol and filtered, and thus a powder-like solid was formed. After this powder-like solid was repeatedly washed with methanol and water, the powder-like solid was dried at 100° C. under reduced pressure for 8 hours, and thus a powder-like solid was produced (diamine (1), compound represented by the following formula, yield: 95%). The produced powder-like solid was subjected to GPC measurement (solvent: THF, calibrated with standard polystyrene), and thus determined number average molecular weight was 2070, weight average molecular weight was 3500, and average degree of polymerization (m-1) was 5.8.

[Chem. 15]

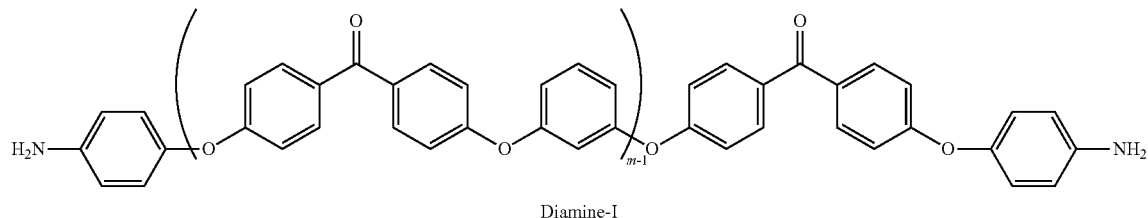

Diamine-1

Preparation Example 2 (Production of Diamine (2))

In a 500 mL (three-necked) flask equipped with an agitation apparatus, a nitrogen introducing tube, and Dean-Stark apparatus, 27.50 g of 4,4'-difluorobenzophenone, 23.98 g of bisphenol A, 21.77 g of anhydrous potassium carbonate ($K_2CO_3$), 220 mL of N-methyl-2-pyrrolidone, and 110 mL of toluene were charged and heated while agitated in a nitrogen atmosphere, and the toluene was refluxed at 130 to 140° C. for 4 hours. Thereafter, further heating was performed to distill off the toluene at 170 to 180° C. Furthermore, after the agitation was continued for 10 hours at 170 to 180° C., the temperature was lowered to room temperature.

In the flask containing the product, 5.04 g of 4-aminophenol, 6.39 g of anhydrous potassium carbonate, 30 mL of N-methyl-2-pyrrolidone, and 150 mL of toluene were added and heated again while agitated in a nitrogen atmosphere, and the toluene was refluxed at 130 to 140° C. for 3 hours. Thereafter, heating was performed to distill off the toluene at 170 to 180° C., and agitation was continued for 4 hours while the temperature of 170 to 180° C. was further maintained. The mixture was then cooled to room temperature, and the reaction solution was added to 3000 mL of methanol and filtered, and thus a powder-like solid was formed. After this powder-like solid was repeatedly washed with methanol and water, the powder-like solid was dried at 100° C. under reduced pressure for 8 hours, and thus a powder-like solid was produced (diamine (2), compound represented by the following formula, yield: 95%). The produced powder-like solid was subjected to GPC measurement (solvent: THF, calibrated with standard polystyrene), and thus determined number average molecular weight was 2920, weight average molecular weight was 5100, and average degree of polymerization (m-2) was 6.2.

[Chem. 16]

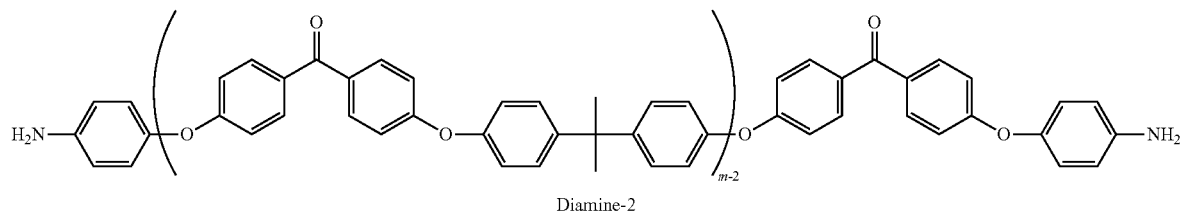

Diamine-2

Example 1 (Production of Curable Compound A)

Figure 5:
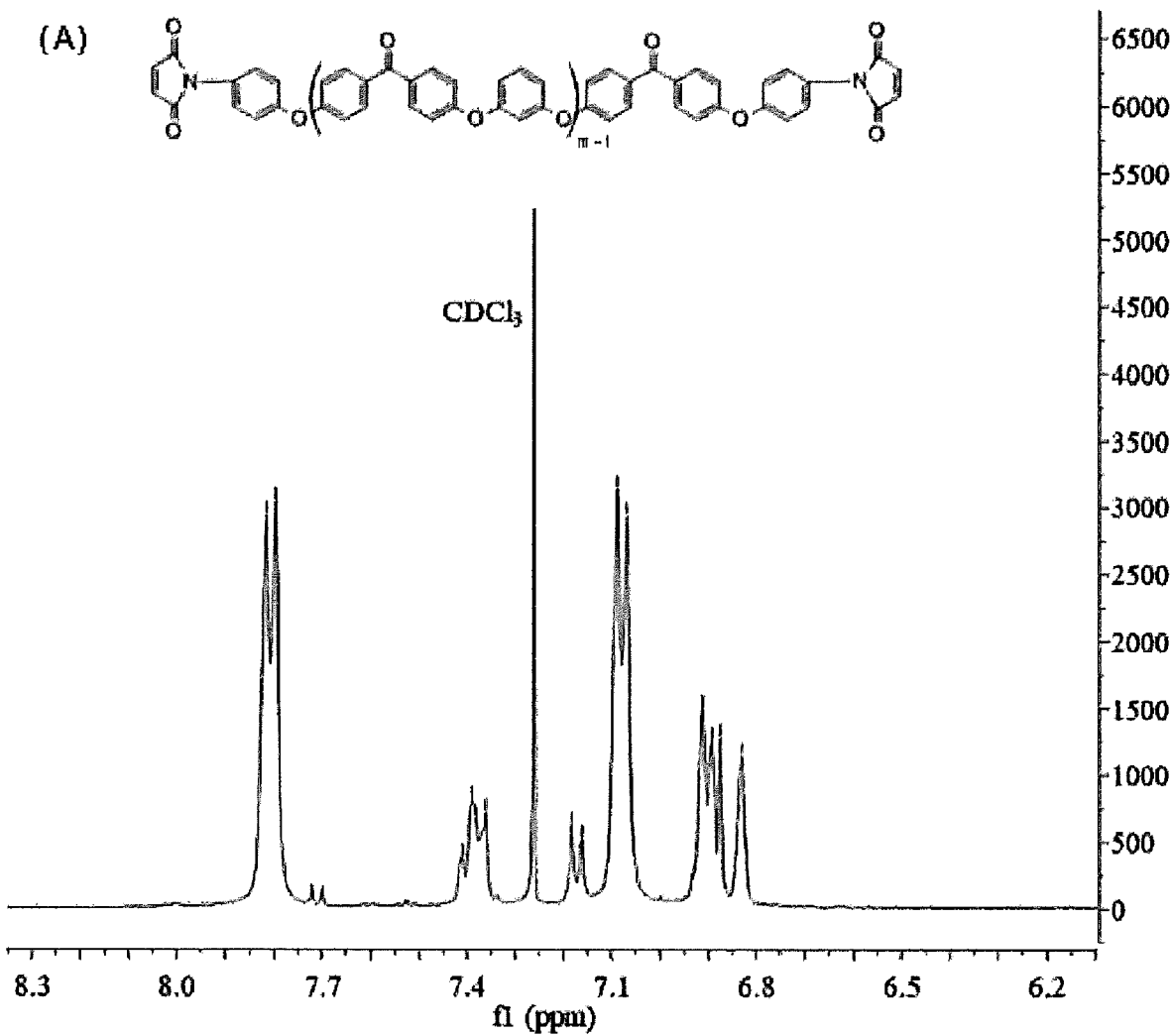
FIG. 5 is a figure showing a $^1$H-NMR spectrum (CDCl$_3$) of a curable compound A produced in Example.
Figure 6:
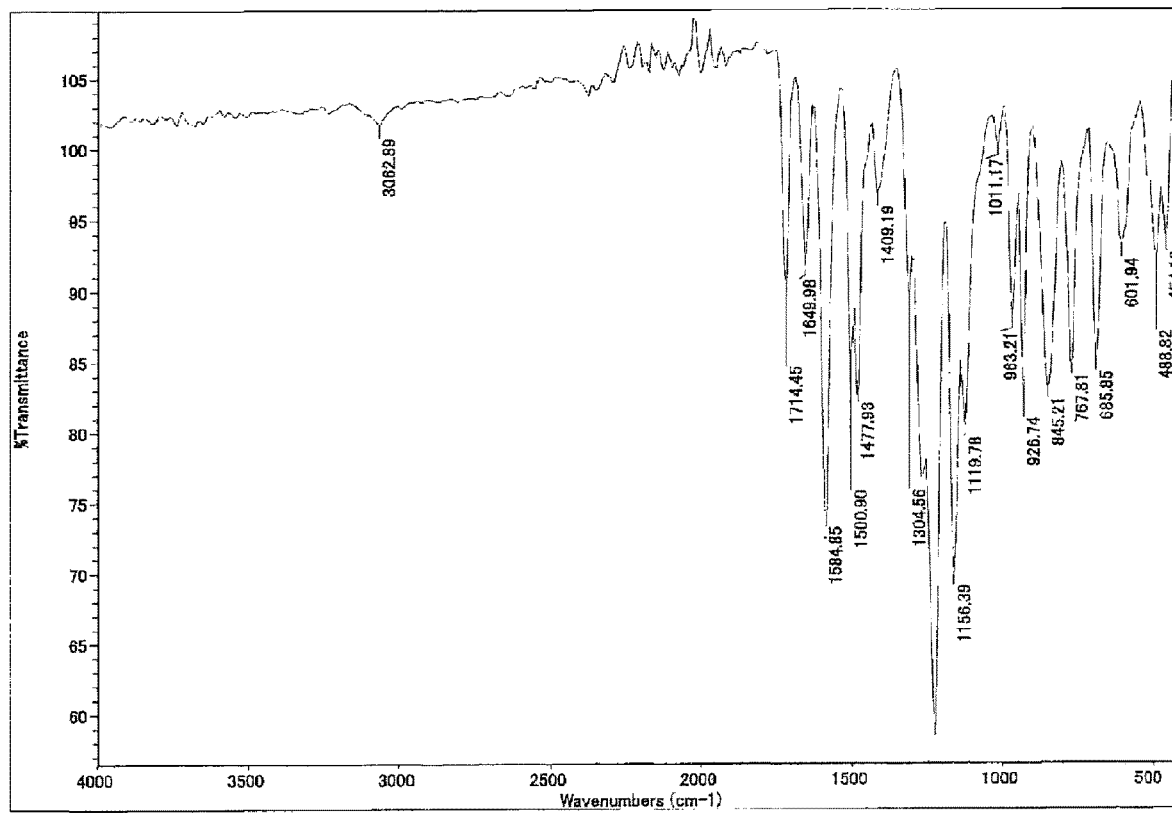
FIG. 6 is a figure showing an FTIR spectrum of a curable compound A produced in Example.

In a 1000 mL (three-necked) flask equipped with an agitation apparatus, a nitrogen introducing tube, and a drying tube, 5.88 g of maleic anhydride, 50 mL of N-methyl-2-pyrrolidone, and 200 mL of toluene were charged, and nitrogen was purged. A solution prepared by dissolving 26.76 g of the diamine (1) prepared in Preparation Example 1 in 250 mL of NMP was added thereto and agitated at room temperature in a nitrogen atmosphere for 24 hours. Thereafter, 0.761 g of p-toluenesulfonic acid monohydrate was added and heated to 140° C., and agitation was continued for 8 hours, and the toluene was refluxed and water was removed. After the reaction solution was cooled to room temperature, and the reaction solution was added to 3000 mL of methanol and filtered, and thus a powder-like solid was formed. After this powder-like solid was repeatedly washed with methanol and water, the powder-like solid was dried at 100° C. under reduced pressure for 8 hours, and thus a powder-like solid was produced (curable compound A, compound represented by Formula (A) below, proportion of aromatic ring-derived structure: 72 wt. %, yield: 90%). The $^1$H-NMR spectrum of the curable compound A is shown in FIG. 5, and the FTIR spectrum is shown in FIG. 6.

Note that the proportion of the structure derived from an aromatic ring was determined by $^1$H-NMR.

$^1$H-NMR (CDCl$_3$) δ: 6.88 (m), 7.08 (d, J=8.0 Hz), 7.17 (d, J=8.0 Hz), 7.39 (m), 7.81 (d, J=8.0 Hz)

[Chem. 17]

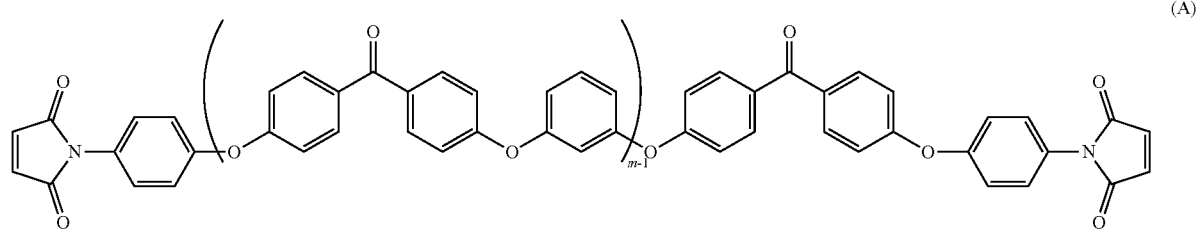

(A)

Furthermore, when the viscosity at 200° C. of the curable compound A was measured by a rheometer, the viscosity was 7 Pa·s.

Example 2 (Production of Curable Compound B)

Figure 7:
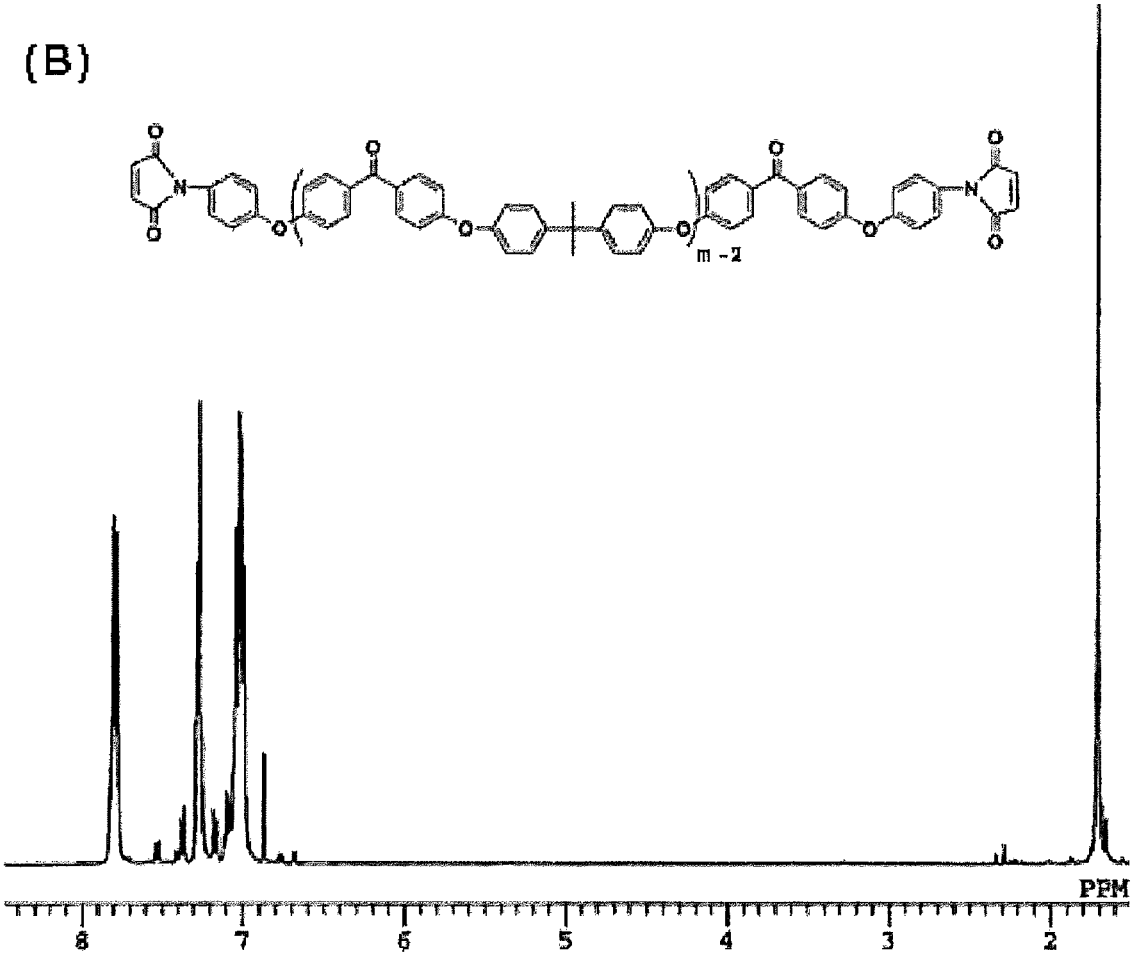
FIG. 7 is a figure showing a $^1$H-NMR spectrum (CDCl$_3$) of a curable compound B produced in Example.
Figure 8:
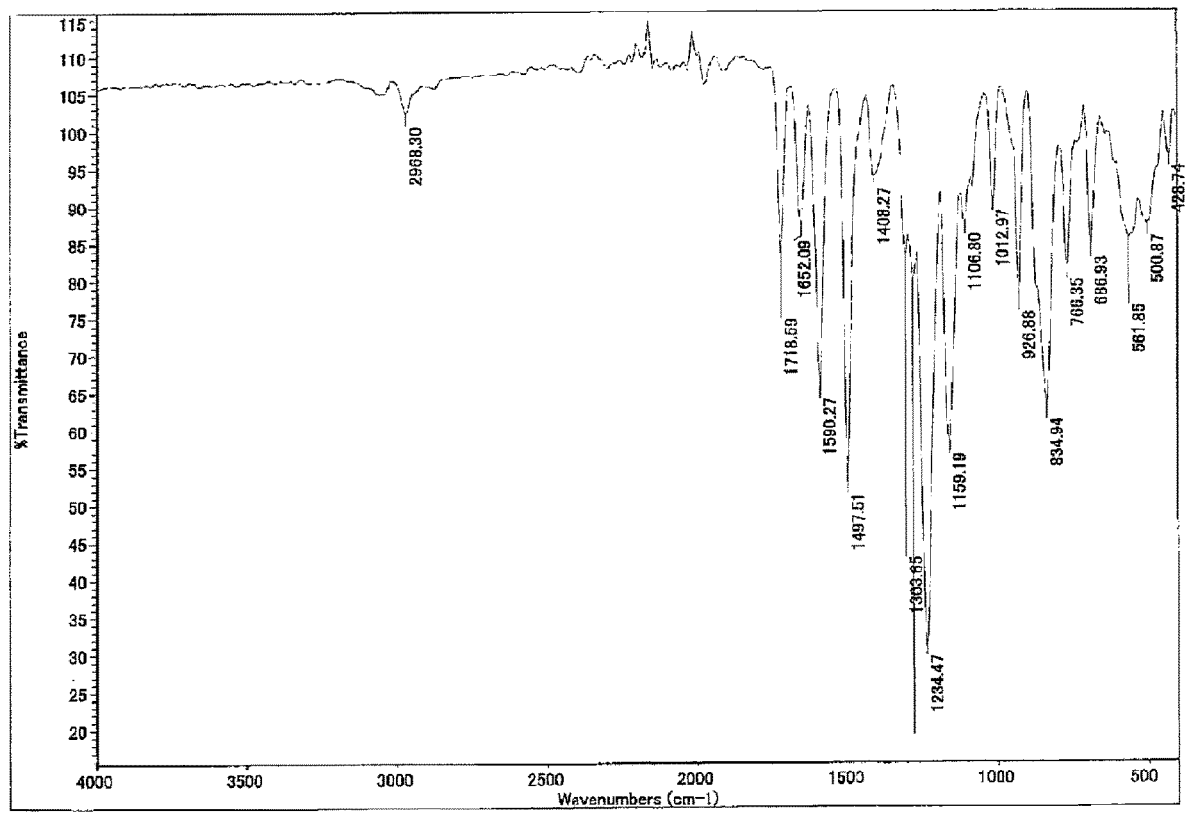
FIG. 8 is a figure showing an FTIR spectrum of a curable compound B produced in Example.

A powder-like solid (curable compound B, compound represented by Formula (B) below, proportion of aromatic ring-derived structure: 71 wt. %, yield: 90%) was produced in the same manner as in Example 1 except that the diamine (2) prepared in Preparation Example 2 was used in place of the diamine (1) and a solution prepared by dissolving 48.57 g of the diamine (2) in 330 mL of NMP was used. The $^1$H-NMR spectrum of the curable compound B is shown in FIG. 7, and the FTIR spectrum is shown in FIG. 8.

$^1$H-NMR (CDCl$_3$) δ: 1.71 (s), 6.87 (s), 7.02 (m), 7.09 (m), 7.17 (d, J=8.8 Hz), 7.26 (m), 7.37 (d, J=8.8 Hz), 7.80 (m)

[Chem. 18]

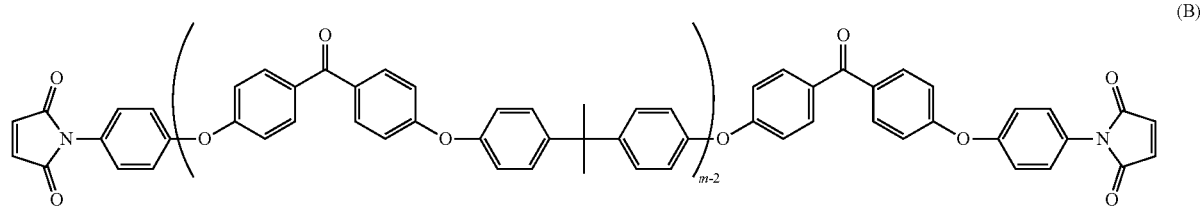

(B)

Furthermore, when the viscosity at 200° C. of the curable compound B was measured by a rheometer, the viscosity was 14 Pa·s.

Example 3 (Synthesis of Curable Compound C)

Figure 9:
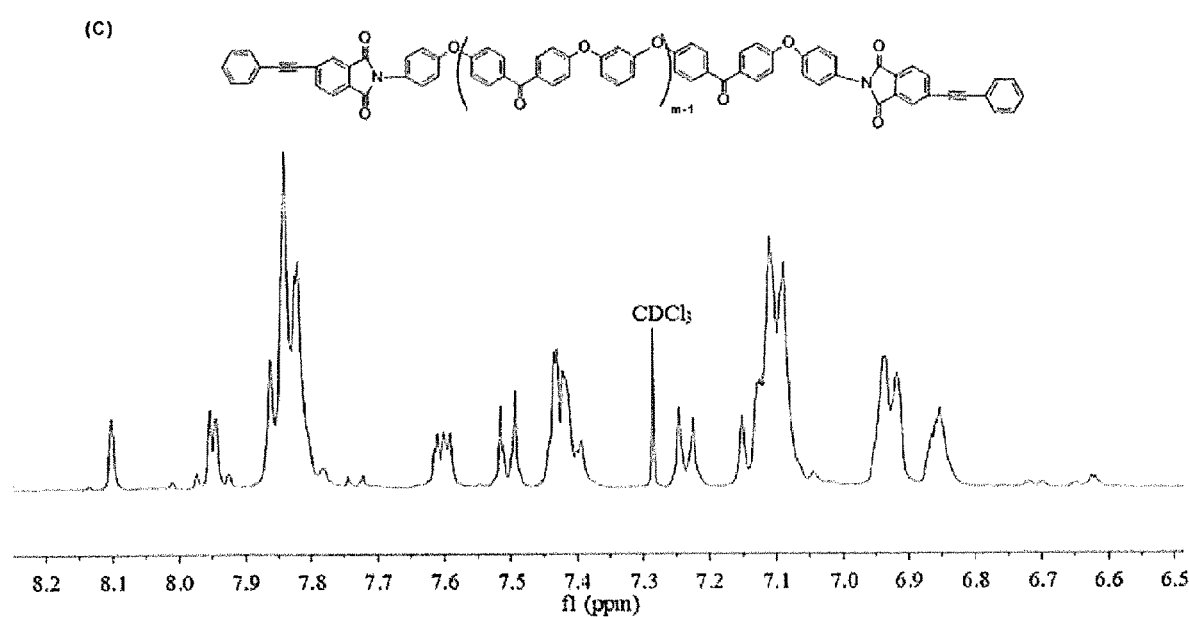
FIG. 9 is a figure showing a $^1$H-NMR spectrum (CDCl$_3$) of a curable compound C produced in Example.
Figure 10:
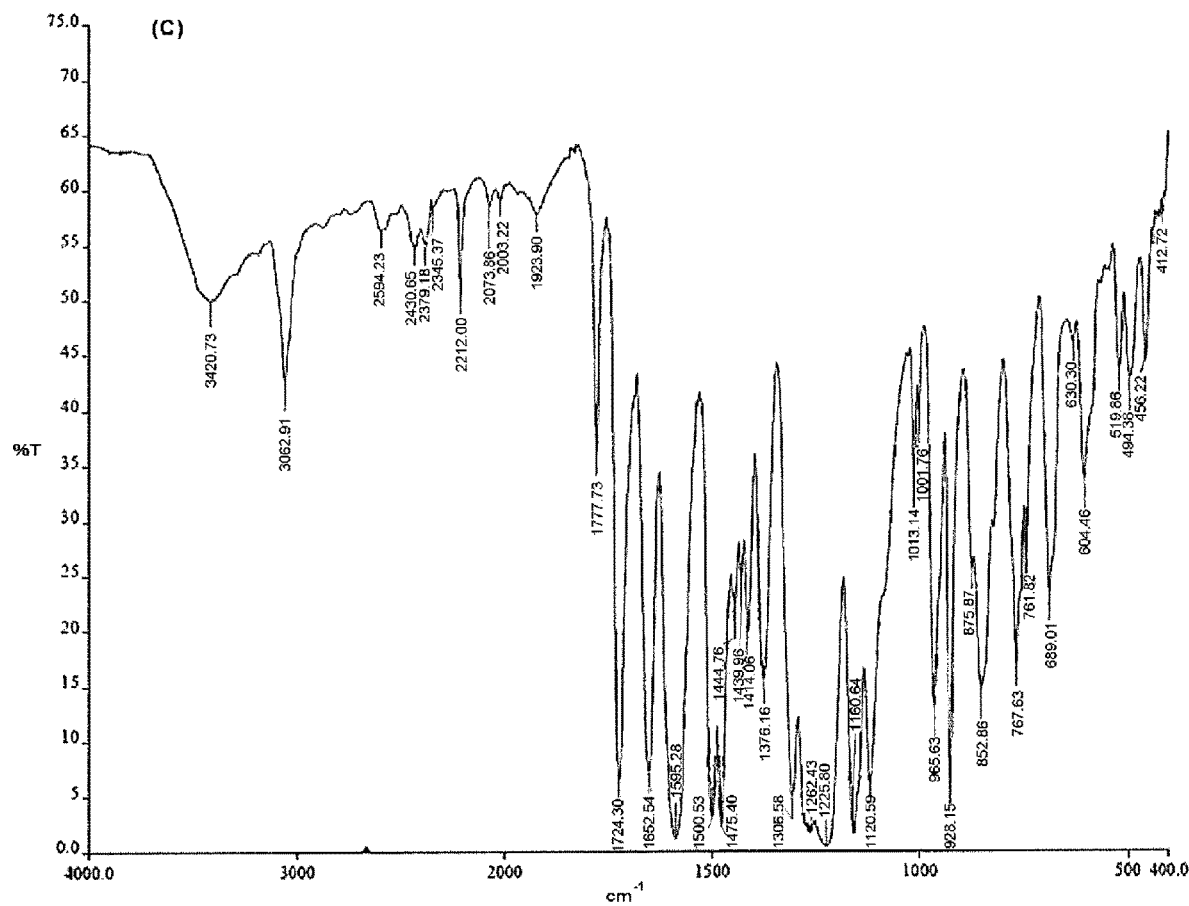
FIG. 10 is a figure showing an FTIR spectrum of a curable compound C produced in Example.

In a 50 mL (three-necked) flask equipped with an agitation apparatus, a nitrogen introducing tube, and a drying tube, 4.571 g of the diamine (1) prepared in Preparation Example 1, 1.852 g of 4-phenylethynyl-phthalic anhydride, and 33 mL of N-methyl-2-pyrrolidone were charged and agitated at room temperature in a nitrogen atmosphere for 24 hours. Then, 4.215 g of acetic anhydride and 1.405 g of triethylamine were added and agitated at 60° C. for 6 hours. After the reaction solution was cooled to room temperature, and the reaction solution was added to 1500 mL of ethanol and filtered, and thus a powder-like solid was formed. After this powder-like solid was repeatedly washed with ethanol and water, the powder-like solid was dried at 100° C. under reduced pressure for 8 hours, and thus a powder-like solid was produced (curable compound C, compound represented by Formula (C) below, proportion of aromatic ring-derived structure: 76 wt. %, yield: 90%). The $^1$H-NMR spectrum of the curable compound C is shown in FIG. 9, and the FTIR spectrum is shown in FIG. 10.

Evaluation

The following evaluations were performed for the curable compounds A, B, C, and D produced in the examples.

Number Average Molecular Weight, Weight Average Molecular Weight

The number average molecular weight and the weight average molecular weight of each of the curable compounds A, B, C, and D produced in the examples were determined by GPC measurement (solvent: THF, calibrated with standard polystyrene).

Tg

The Tg of each of the curable compounds A, B, C, and D produced in the examples was determined by DSC measurement.

Figure 13:
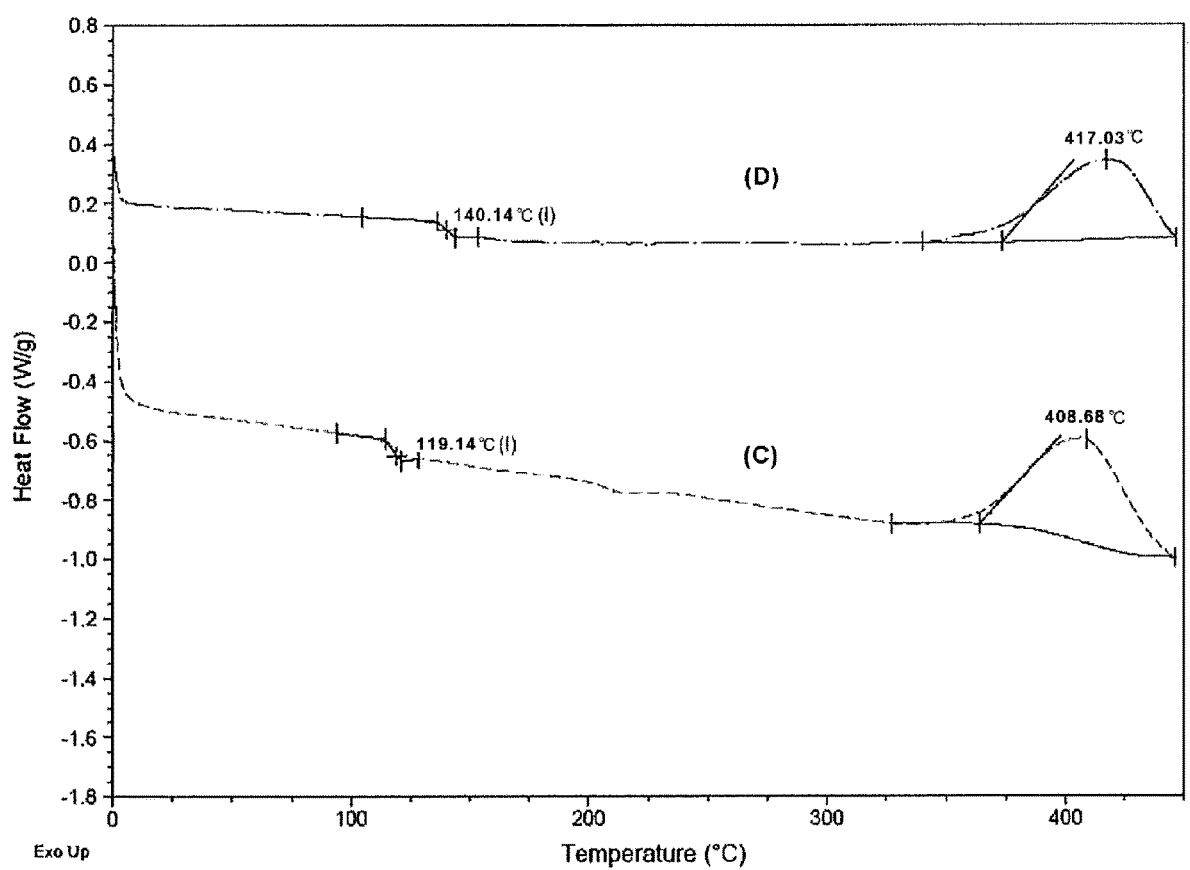
FIG. 13 is a figure showing DSC measurement results of curable compounds C and D produced in Examples.

The DSC measurement results of the curable compounds C and D are shown in FIG. 13. The Tg of the curable compound D was approximately 140° C., the Tg of the curable compound C was approximately 120° C., and exothermic peaks by the curing reaction were observed around 400° C. for both the curable compounds C and D.

Thermogravimetric Analysis of Cured Product

Each of the curable compound A, B, C, or D produced in the examples or PEEK as a comparative example was placed on a glass plate to have a uniform thickness of approxi-

[Chem. 19]

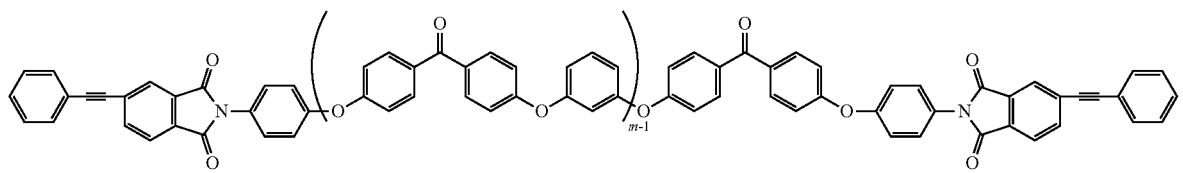

(C)

$^1$H-NMR (CDCl$_3$) δ: 6.83 (m), 6.90 (m), 7.09 (m), 7.21 (d, J=8.8 Hz), 7.39 (m), 7.48 (d, J=8.8 Hz), 7.58 (m), 7.81 (m), 7.92 (m), 8.08 (s)

Example 4 (Synthesis of Curable Compound D)

Figure 11:
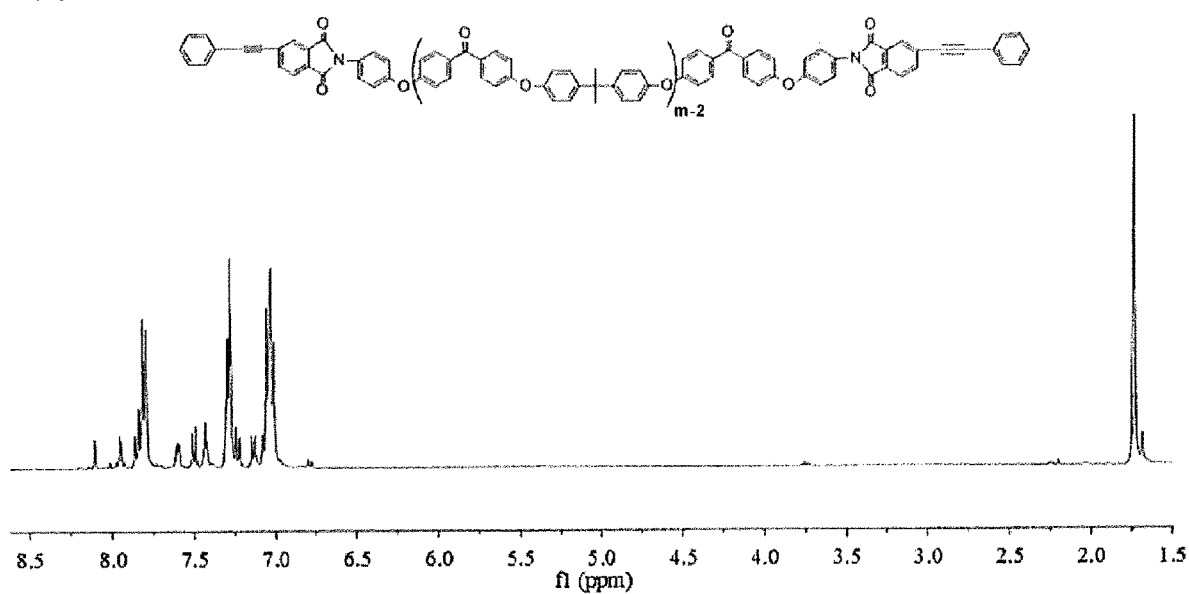
FIG. 11 is a figure showing a $^1$H-NMR spectrum (CDCl$_3$) of a curable compound D produced in Example.
Figure 12:
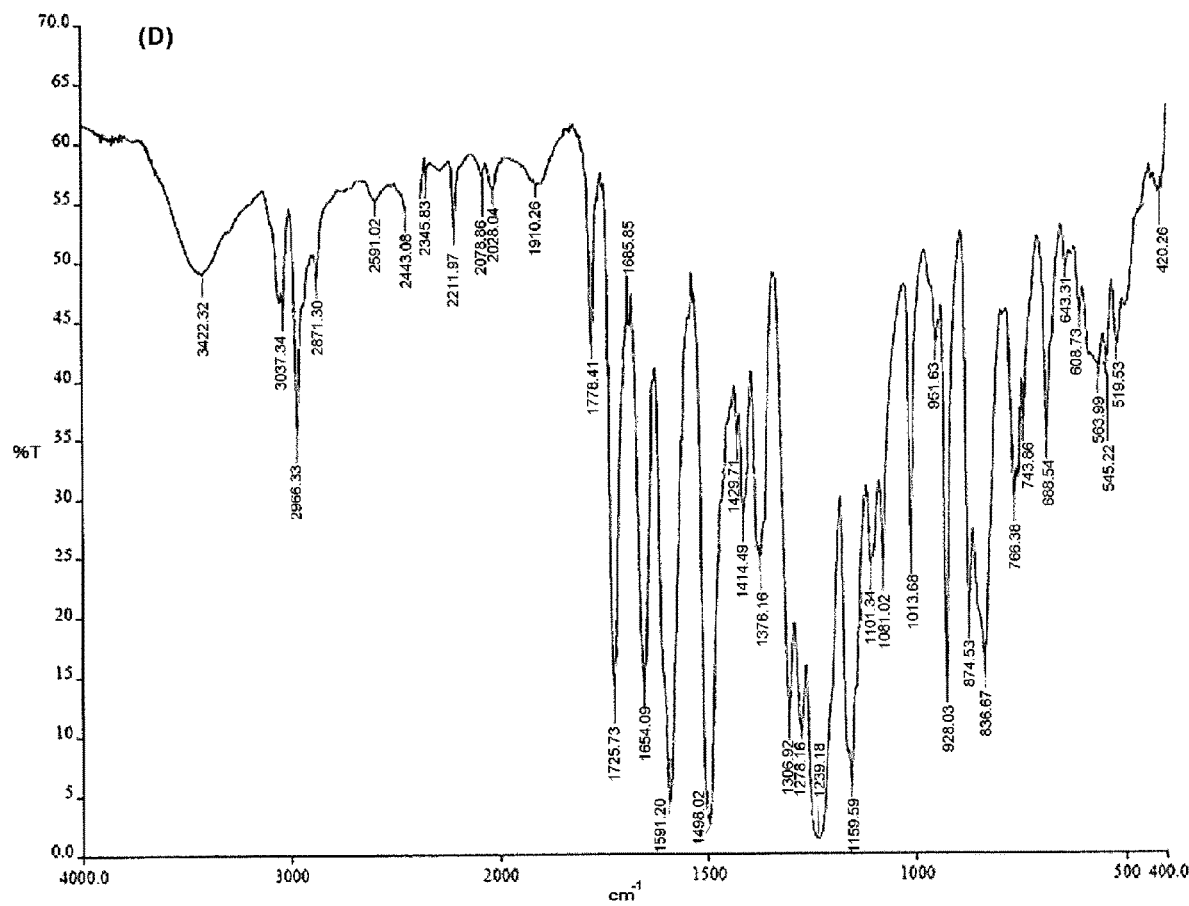
FIG. 12 is a figure showing an FTIR spectrum of a curable compound D produced in Example.

A powder-like solid (curable compound D, compound represented by Formula (D) below, proportion of aromatic ring-derived structure: 74 wt. %, yield: 90%) was formed in the same manner as in Example 3 except that the diamine (2) prepared in Preparation Example 2 was used in place of the diamine (1), 4.550 g of the diamine (2) was used, and 1.395 g of 4-phenylethynyl-phthalic anhydride was used. The $^1$H-NMR spectrum of the curable compound D is shown in FIG. 11, and the FTIR spectrum is shown in FIG. 12.

mately 0.5 mm, and heated and cured in a muffle furnace (temperature was increased from 25° C. to 371° C. at 10° C./min and then maintained at 371° C. for 2 hours), and a cured product was produced.

Figure 14:
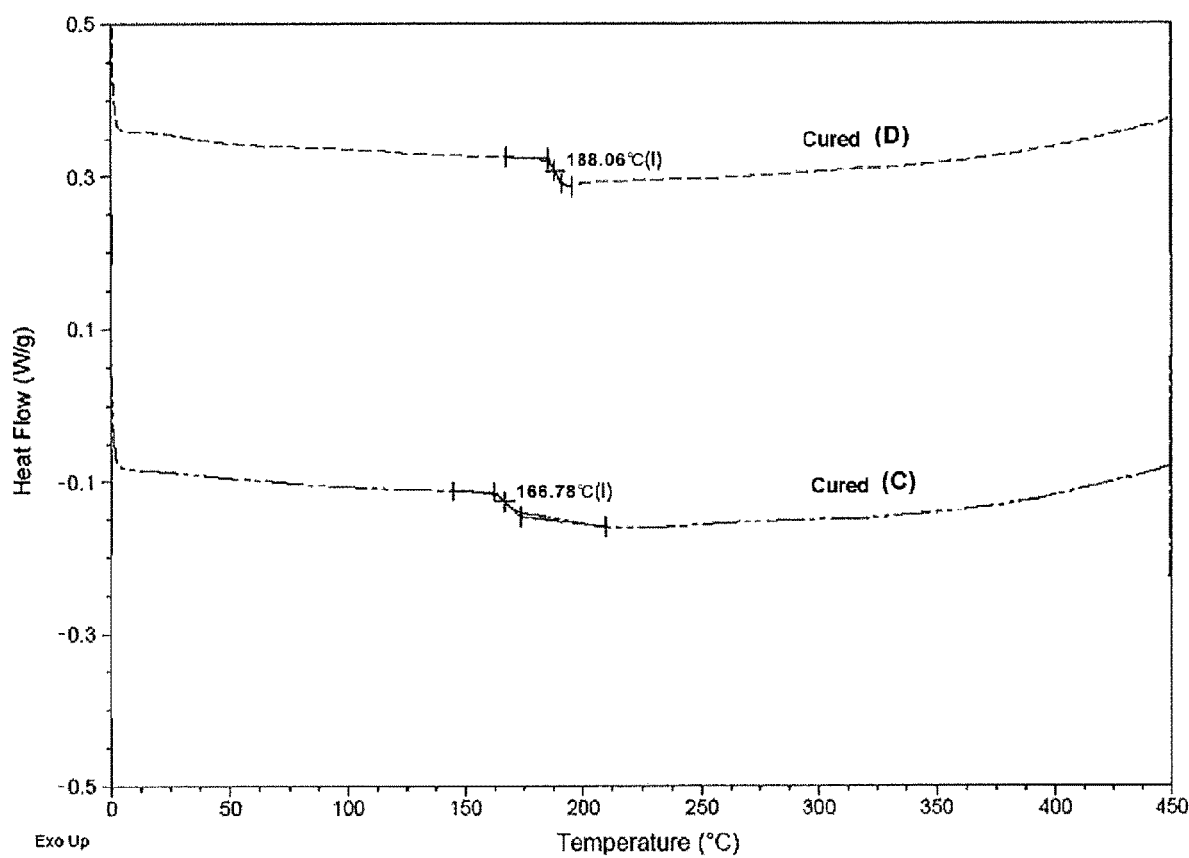
FIG. 14 is a figure showing DSC measurement results of cured products of curable compounds C and D produced in Examples.

The DSC results of the cured product of the curable compound C and the cured product of the curable compound D are shown in FIG. 14. Because no exothermic peaks were observed in the DSC chart, it was found that the produced cured product had high degree of curing (or the curable compound produced in the examples exhibited excellent curability and lost all the curable functional groups by heat treatment).

Furthermore, the thermogravimetric analysis of the cured product was performed by using a TG/DTA, and the 5%

[Chem. 20]

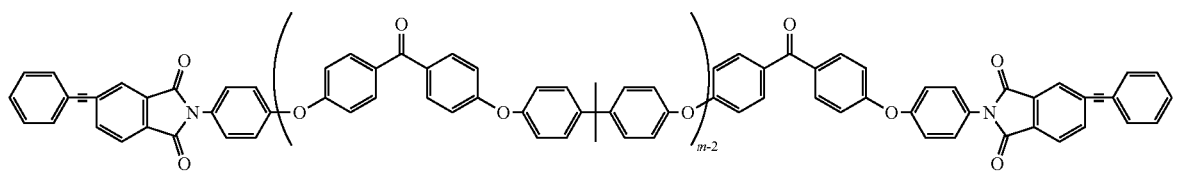

(D)

Figure 15:
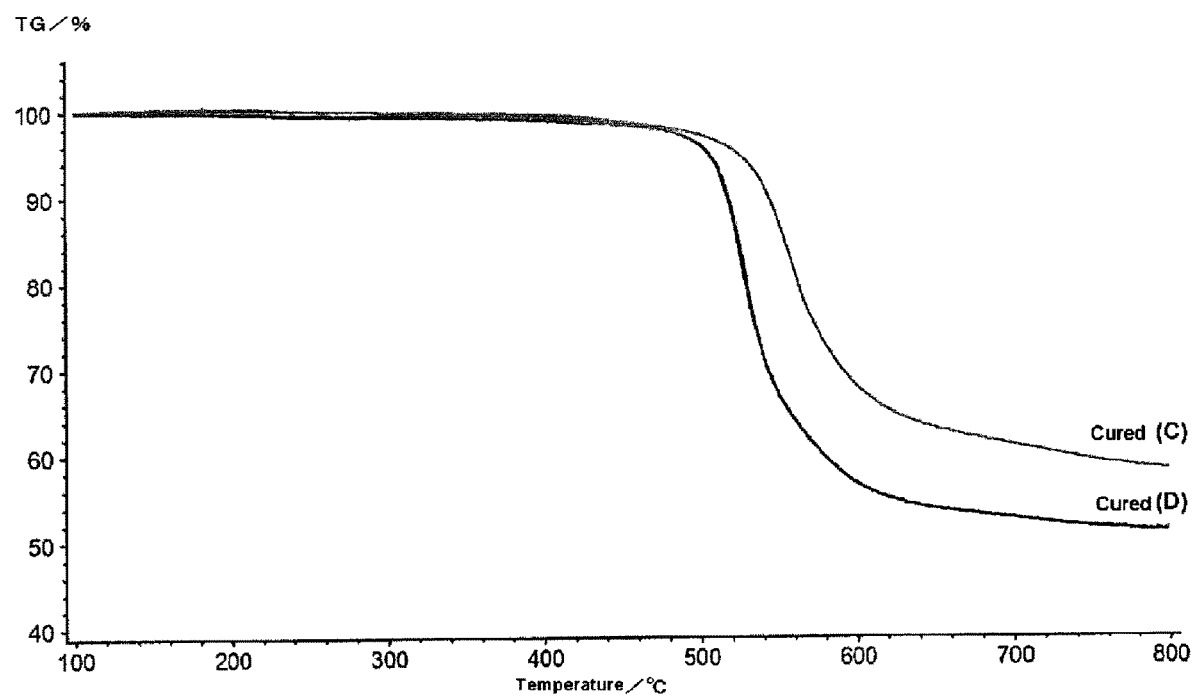
FIG. 15 is a figure showing thermogravimetric analysis results of cured products of curable compounds C and D produced in Examples.

$^1$H-NMR (CDCl$_3$) δ: 1.71 (s), 7.02 (m), 7.11 (d, J=8.8 Hz), 7.21 (d, J=8.8 Hz), 7.27 (m), 7.41 (m), 7.48 (d, J=8.8 Hz), 7.58 (m), 7.81 (m), 7.93 (m), 8.08 (s)

weight loss temperature (T$_{d5}$) and 10% weight loss temperature (T$_{d10}$) were determined. The thermogravimetric analysis results of the cured product of the curable compound C and the cured product of the curable compound D are shown in FIG. 15.

Nitrogen Atom Content

Each of the curable compound A, B, C, or D produced in the examples or PEEK as a comparative example was subjected to CHN elemental analysis, and the nitrogen atom content was determined. Note that antipyrine was used as a reference material.

The results are summarized and shown in the table below.
[Table 1]

TABLE 1

| Curable compound | Number average molecular weight (Mn) | Weight average molecular weight (Mw) | Tg (° C.) | N content of curable compound (wt. %) | $T_{d5}$ of cured product (° C.) | $T_{d10}$ of cured product (° C.) |
|---|---|---|---|---|---|---|
| Curable compound A | 2400 | 3525 | 107 | 1.28 | 512 | 528 |
| Curable compound B | 3160 | 5190 | 131 | 0.97 | 501 | 525 |
| Curable compound C | 2700 | 4170 | 120 | — | 539 | 553 |
| Curable compound D | 3840 | 6630 | 142 | — | 505 | 517 |
| PEEK | — | — | 147 | <0.3 | 559 | — |

Solvent Solubility Evaluation

The solvent solubility was measured by the following method.

Each (1 g) of the curable compound A, B, C, or D produced in the examples or PEEK as a comparative example was mixed in a solvent (100 g) shown in the following table and agitated at 25° C. for 24 hours, and the solubility in the solvent was evaluated based on the following criteria.

Evaluation Criteria

Good: Completely dissolved

Poor: At least a portion remained undissolved

The results are summarized and shown in the table below.
[Table 2]

TABLE 2

| Curable compound | Solvent | | | |
| | NMP | DMSO | Chloroform | THF |
|---|---|---|---|---|
| Curable compound A | Good | Good | Good | Good |
| Curable compound B | Good | Good | Good | Good |
| Curable compound C | Good | Good | Good | Good |
| Curable compound D | Good | Good | Good | Good |
| PEEK | Poor | Poor | Poor | Poor |

Solvent NMP: N-methyl-2-pyrrolidone
DMSO: dimethyl sulfoxide
THF: tetrahydrofuran Bonding Strength Evaluation Each of the curable compound A, B, C, or D produced in the examples was placed on a substrate shown in the following table to have a uniform thickness of approximately 0.5 mm, and heated and cured under the conditions shown in the following table, and a cured product/substrate laminate was produced.

The bonding strength of the cured product to the substrate of the produced laminate was evaluated by measuring a maximum stress by a method in accordance with JIS K 6850.

The results are summarized and shown in the table below.
[Table 3]

TABLE 3

| | Used amount (mg) | Substrate | Heating conditions | | Maximum stress (MPa) |
| | | | Temperature and time | Pressure (MPa) | |
|---|---|---|---|---|---|
| Curable compound A | 7.8 | Aluminum | 160° C. 30 min → 230° C. 60 min | 1 | 25.43 |
| Curable compound B | 5.4 | Aluminum | 175° C. 30 min → 230° C. 60 min | 1.8 | 25.23 |
| Curable compound C | 11.0 | Stainless steel | 230° C. 30 min → 370° C. 60 min | 0.5 to 1 | 27.00 |
| Curable compound D | 18.5 | Stainless steel | 230° C. 30 min → 370° C. 60 min | >3 | 25.26 |

Substrate Aluminum: A5052
Stainless steel: SUS304

Examples 5 to 16 (Paint)

The curable compound and the solvent were weighed into a sample vial as shown in Table 4 below and agitated. The curable compound was completely dissolved by application of ultrasonic waves at 25° C. for 5 minutes, and a paint was produced.

The produced paint was casted on a substrate using a syringe and uniformly spread using an applicator, and this was subjected to primary drying (drying in a drier at 120° C. for 1 hour) and then secondary drying (drying in a drier at 150° C. in a vacuum for 1 hour), and thus a coated film was produced. The produced coated film was subjected to heat-curing (in a drier at 220° C. in a vacuum for 1 hour), and a cured product/substrate laminate was produced.

Comparative Example 1 (Paint)

In the case where PEEK was used as the curable compound, the PEEK was not dissolved in the solvent even after heated and agitated at 140° C. for 5 minutes, and a paint could not be formed.

Examples 11-2 and 11-3

Paints and cured product/substrate laminates were produced in the same manner as in Example 11 except for the following changes.

That is, fillers were added as shown in Table 5 below. Furthermore, the heat curing conditions of the paint were changed to "in a drier at 300° C. in a vacuum for 1 hour".

Examples 17 to 21 (Powder Coating Agent)

As shown in Table 6 below, each of the curable compounds was used as a powder coating agent, and this was placed on a substrate and uniformly spread, and melted by being heated at 250° C. for 5 minutes, and a coated film was formed. The produced coated film was subjected to heat-curing (heated in a drier at 320° C. for 30 minutes), and a cured product/substrate laminate was produced.

Comparative Example 2 (Powder Coating Agent)

In the case where PEEK was used as the curable compound, the PEEK did not melt even after heated at 320° C. for 60 minutes, and a coated film could not be formed.

Each of the cured product/substrate laminates produced in Examples 5 to 21, 11-2, and 11-3, and Comparative Examples 1 and 2 was subjected to Cross Cut Tape Test (in accordance with JIS K 5400-8.5), and adhesion of the cured product to the substrate was evaluated based on the following criteria.

Good: No peeling of the cured product was observed
Poor: Peeling of the cured product was observed
The results are summarized and shown in the table below.

[Table 4]

TABLE 4

| | | Example 5 | Example 6 | Example 7 | Example 8 | Example 9 | Example 10 | Example 11 | Example 12 | Example 13 | Example 14 | Example 15 | Example 16 | Comparative Example 1 |
|---|---|---|---|---|---|---|---|---|---|---|---|---|---|---|
| Paint | Curable compound | A | A | A | A | A | A | B | B | B | B | B | B | PEEK |
| | Curable compound concentration (wt %) | 10 | 10 | 10 | 10 | 10 | 10 | 20 | 20 | 20 | 20 | 20 | 20 | 10 |
| | Solvent | NMP | NMP | NMP | NMP | NMP | NMP | NMP | NMP | NMP | NMP | NMP | NMP | NMP |
| Substrate | | Copper foil | Stainless steel | Aluminum | Glass | Silicon wafer | Polyimide | Copper foil | Stainless steel | Aluminum | Glass | Silicon wafer | Polyimide | Poor |
| Adherence | | Good | Good | Good | Good | Good | Good | Good | Good | Good | Good | Good | Good | Poor |

[Table 5]

TABLE 5

| | | Example 11-2 | Example 11-3 |
|---|---|---|---|
| Paint | Curable compound | B | B |
| | Curable compound concentration (wt. %) | 20 | 20 |
| | Solvent | NMP | NMP |
| | Filler | Silica | Mica |
| | Filler concentration (wt. %) | 5 | 5 |
| | Substrate | Copper foil | Copper foil |
| | Adherence | Good | Good |

Solvent NMP: N-methyl-2-pyrrolidone
Substrate Copper foil: commercially available electrolytic copper foil, Rz=0.85 μm
Stainless steel: SUS430
Aluminum: aluminum cup with handle
Glass: MICRO SLIDE GLASS S1214
Polyimide: Kapton H, available from Du Pont-Toray Co., Ltd.
Silica: HS-207, available from NIPPON STEEL Chemical & Material Co., Ltd.
Mica: NK-8G, available from Nihon Koken Kogyo Co., Ltd.

[Table 6]

TABLE 6

| | | Example 17 | Example 18 | Example 19 | Example 20 | Example 21 | Comparative Example 2 |
|---|---|---|---|---|---|---|---|
| Powder coating agent | Curable compound | B | B | B | B | B | PEEK |
| | Curable compound concentration (wt. %) | — | — | — | — | — | — |
| | Solvent | — | — | — | — | — | — |
| | Substrate | Copper foil | Aluminum | Glass | Polyimide | SUS403 | Glass |
| Melting | Heating temperature (° C.) | 250 | 250 | 250 | 250 | 250 | 320 |
| | Heating time (min) | 5 | 5 | 5 | 5 | 5 | 60 |
| | Adherence | Good | Good | Good | Good | Good | Poor |

Examples 22 to 25 (Sealing Agent)

The curable compound and the solvent were weighed into a sample vial as shown in Table 7 below and agitated. The curable compound was completely dissolved by application of ultrasonic waves at 25° C. for 5 minutes, and a sealing agent was produced.

The produced sealing agent was casted on a substrate using a syringe and uniformly spread using an applicator, and this was subjected to primary drying (drying in a drier at 120° C. for 1 hour) and then secondary drying (drying in a drier at 150° C. in a vacuum for 1 hour), and thus a coated film was produced. The produced coated film was subjected to heat-curing (in a drier at 220° C. in a vacuum for 1 hour), and a cured product/substrate laminate was produced.

Comparative Example 3 (Sealing Agent)

In the case where PEEK was used as the curable compound, the PEEK was not dissolved in the solvent even after heated and agitated at 140° C. for 5 minutes, and a sealing agent could not be formed.

Each of the cured product/substrate laminates produced in Examples 22 to 25 and Comparative Example 3 and the cured product/substrate laminates after being subjected to heat resistance test (heated at 270° C. for 1 hour) was subjected to Cross Cut Tape Test (in accordance with JIS K 5400-8.5), and adhesion of the cured product to the substrate was evaluated based on the following criteria.

Good: No peeling of the cured product was observed
Poor: Peeling of the cured product was observed For each of the cured product/substrate laminates produced in Examples 22 to 25 and Comparative Example 3, the relative permittivity and the dielectric loss tangent of the cured product were measured by the method described below Measurement Method A test piece having a width of 1.5 mm was prepared by cutting the cured product/substrate laminate, and the relative permittivity and the dielectric loss tangent were measured by a resonant cavity perturbation method (in accordance with ASTM D2520). The measurement was performed at a frequency of 10 GHz.

The results are summarized and shown in the table below.
[Table 7]

Examples 26 to 27 (Laminate)

The curable compound and the solvent were weighed into a sample vial as shown in Table 8 below and agitated. The curable compound was completely dissolved by application of ultrasonic waves at 25° C. for 5 minutes, and a composition was produced.

The produced composition was casted on a substrate (1) using a syringe and uniformly spread using an applicator, and this was subjected to primary drying (drying in a drier at 120° C. for 1 hour) and then secondary drying (drying in a drier at 150° C. in a vacuum for 1 hour), and thus a coated film was produced. The produced coated film was subjected to heat-curing (in a drier at 220° C. in a vacuum for 1 hour), and a cured product/substrate (1) laminate was produced.

Comparative Example 4 (Laminate)

In the case where PEEK was used as the curable compound, the PEEK was not dissolved in the solvent even after heated and agitated at 140° C. for 5 minutes. Thus, adhesion to the substrate (1) could not be performed, and thus a PEEK cured product/substrate (1) laminate could not be formed.

Example 28 (Laminate)

The curable compound and the solvent were weighed into a sample vial as shown in Table 8 below and agitated. The curable compound was completely dissolved by application of ultrasonic waves at 25° C. for 5 minutes, and a composition was produced.

The produced composition was casted on a substrate (1) using a syringe and uniformly spread using an applicator, and this was subjected to primary drying (drying in a drier at 120° C. for 1 hour) and then secondary drying (drying in a drier at 150° C. in a vacuum for 1 hour), and thus a coated film was produced.

To the produced coated film, a substrate (2) was laminated and then heat-cured (in a drier at 220° C. for 1 hour), and a substrate (2)/cured product/substrate (1) laminate was produced.

Comparative Example 5 (Laminate)

On a film-like PEEK, a substrate (2) was laminated and then heat-treated (3 MPa, in a drier at 300° C. for 1 hour); however, the PEEK did not melt and did not adhere to the

TABLE 7

| | | Example 22 | Example 23 | Example 24 | Example 25 | Comparative Example 3 |
|---|---|---|---|---|---|---|
| Sealing agent | Curable compound | A | A | B | B | PEEK |
| | Curable compound concentration (wt. %) | 10 | 10 | 20 | 20 | 10 |
| | Solvent | NMP | NMP | NMP | NMP | NMP |
| | Substrate | Copper foil | Silicon wafer | Copper foil | Silicon wafer | — |
| Evaluation | Grid peel test (after curing) | Good | Good | Good | Good | — |
| | Grid peel test (after heat resistance test) | Good | Good | Good | Good | — |
| | Relative permittivity | 2.52 | 2.42 | 2.69 | 2.69 | — |
| | Dielectric loss tangent | 0.004 | 0.004 | 0.0049 | 0.0049 | — | substrate (2). Thus, a PEEK cured product/substrate (2) laminate could not be formed.

Example 28-2 (Laminate)

A composition and a substrate (2)/cured product/substrate (1) laminate were produced in the same manner as in Example 28 except for the following changes.

That is, as shown in Table 9 below, a copper foil was used as the substrate (2).

Example 28-3 (laminate)

The composition produced in the same manner as in Example 28 was casted on a carrier (made of polyimide, thickness: 100 μm) and uniformly spread using an applicator, and this was subjected to primary drying (drying in a drier at 120° C. for 1 hour), secondary drying (drying in a drier at 150° C. for 1 hour), and then tertiary drying (drying in a drier at 210° C. in a vacuum for 1 hour), and thus a coated film having a thickness of 100 μm was produced.

The produced coated film was released from the carrier. The coated film was easily released from the carrier.

Using a substrate (1) and a copper foil (thickness: 18 μm) as a substrate (2), heat curing was performed while the coated film was sandwiched between the substrate (1) and the substrate (2) [in a vacuum thermocompression bonding machine, the temperature was increased from 210° C. to 300° C. at 5° C./min, and the temperature was maintained for 60 minutes. After the start of the temperature increase, the pressure was increased to 3 MPa in 5 minutes], and thus a substrate (2)/cured product/substrate (1) laminate was produced.

For each of the laminates produced in Examples 26 to 28, 28-2, and 28-3, flexibility was evaluated by the following method.

That is, the laminate was cut to a size of 1 cm×10 cm and folded in half at the center in the longitudinal direction (5 cm from the end). A 100 g weight was placed on the folded part, and then the appearance of the cured product was visually observed, and evaluation was performed based on the following criteria.

Flexibility evaluation criteria
Good: No cracking or peeling was observed
Poor: Cracking or peeling was observed For each of the laminates produced in Examples 26 to 28, 28-2, and 28-3 (in the case of Examples 28, 28-2, and 28-3, each of the cured product/substrate (1) laminates) was subjected to Cross Cut Tape Test (in accordance with JIS K 5400-8.5), and adhesion of the cured product to the substrate was evaluated based on the number of the squares that were not peeled off and remained among 100 squares.

The relative permittivity and the dielectric loss tangent of each of the cured products of the laminates produced in Examples 26 to 28, 28-2, and 28-3 and the film-like PEEK used in Comparative Example 5 were measured by the same method as described above.

The results are summarized and shown in the table below.

[Table 8]

TABLE 8

|  |  | Example 26 | Example 27 | Example 28 | Comparative Example 4 | Comparative Example 5 |
| --- | --- | --- | --- | --- | --- | --- |
| Composition | Curable compound | A | B | B | PEEK | PEEK (film-like) |
|  | Curable compound concentration (%) | 10 | 20 | 20 | Insoluble | — |
|  | Solvent | NMP | NMP | NMP | NMP | — |
|  | Substrate (1) | Copper foil | Copper foil | Polyimide | — | — |
|  | Substrate (2) | — | — | Copper foil | — | Copper foil |
| Evaluation | Flexibility | Good | Good | Good | — | — |
|  | Grid peel test | 100/100 | 100/100 | 100/100 | — | 0/100 |
|  | Relative permittivity | 2.52 | 2.69 | 2.69 | — | 2.74 |
|  | Dielectric loss tangent | 0.004 | 0.0049 | 0.0049 | — | 0.0029 |

[Table 9]

TABLE 9

|  |  | Example 28-2 | Example 28-3 |
| --- | --- | --- | --- |
| Composition | Curable compound | B | B |
|  | Curable compound concentration (%) | 20 | 20 |
|  | Solvent | NMP | NMP |
|  | Substrate (1) | Copper foil | Copper foil |
|  | Substrate (2) | Copper foil | Copper foil |
|  | Carrier | — | Polyimide |
| Evaluation | Flexibility | Good | Good |
|  | Grid peel test | 100/100 | 100/100 |
|  | Relative permittivity | 2.69 | 2.69 |
|  | Dielectric loss tangent | 0.0049 | 0.0049 |

Examples 29 to 36 (Composite Material)

As described in Table 10 below, the curable compound was dissolved in cyclohexanone, and a composition for composite material formation was produced.

In 5.0 g of the produced composition, 1.186 g of fiber were immersed and allowed to stand still as is at 25° C. for 8 hours. Thereafter, the fiber was taken out from the solution and heated on a hot stage at 130° C. for 1 hour to volatilize the cyclohexanone, and a composite material (prepreg) was produced.

The produced composite material (prepreg) was sandwiched by aluminum foil, placed in a press machine, and heated at 250° C. for 3 minutes, and then a pressure of 0.1 MPa was applied. The temperature was maintained at 250° C. for 8 minutes, then increased to 320° C. for 12 minutes, and maintained at 320° C. for 20 minutes to cure the curable compound, and thus a composite material (cured product) was produced.

Comparative Example 6 (Composite Material)

In the case where PEEK was used as the curable compound, the PEEK was not dissolved in cyclohexanone even after heated and agitated at 140° C. for 5 minutes, and a composition for composite material formation was not produced. Thus, the fiber could not be impregnated with the PEEK.

When a cross-section of each of the composite materials (cured products) produced in Examples 29 to 36 was observed, it was confirmed that the curable compound was incorporated into gaps of 1 μm or less of the fiber and cured.

[Table 10]

Example 38

Figure 17:
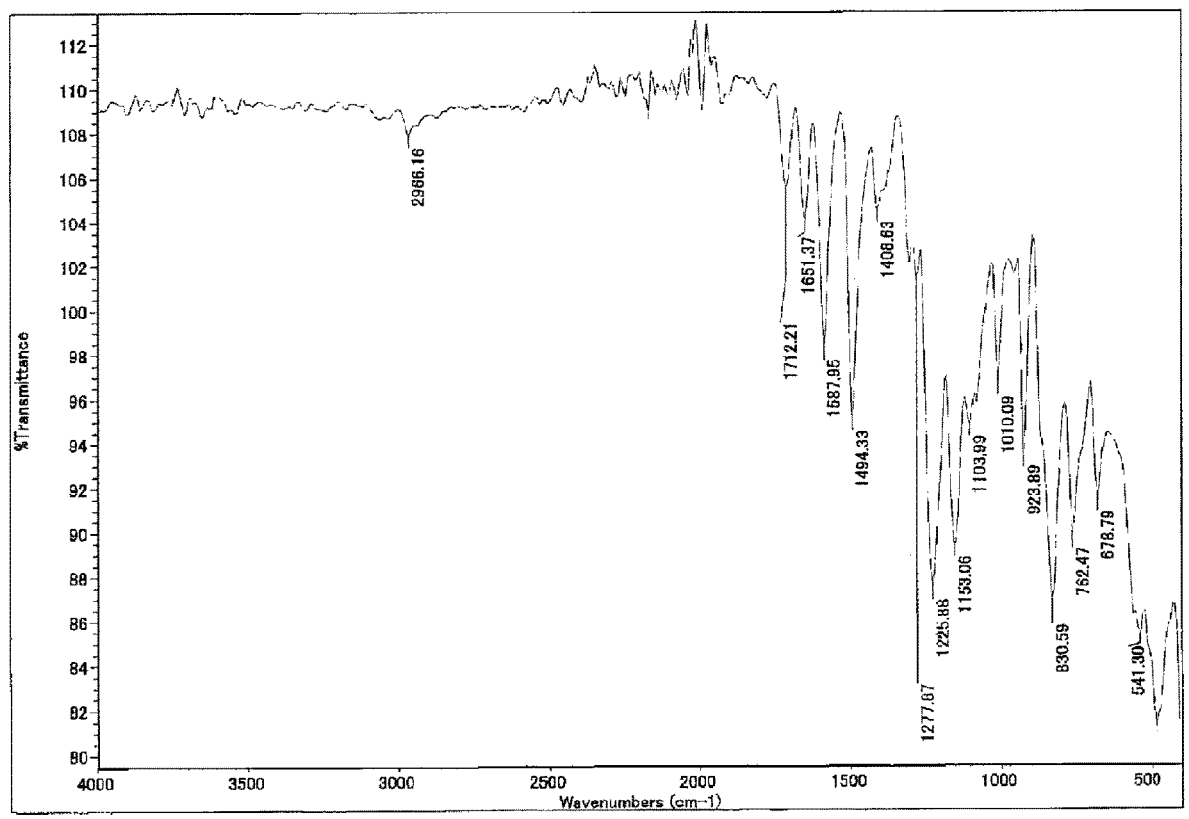
FIG. 17 is a figure showing an FTIR spectrum of a cured product of a curable compound B produced in Example.

A cured product in a planer form (thickness: 0.2 cm) was produced in the same manner as in Example 37 except for using the curable compound B in place of the curable compound A. The FTIR spectrum of the produced cured product is shown in FIG. 17. The physical properties of the produced cured product were as follows.

Density (JIS K7112A 23° C.): 1.19 g/cm$^3$
Glass transition temperature (measured by DSC): 176° C.
Thermal expansion coefficient (according to JIS K 7197) (Tg or lower): 73 ppm/° C.
Thermal expansion coefficient (according to JIS K 7197) (Tg or higher): 234 ppm/° C.
Relative permittivity (according to JIS-C2138, 23° C.) (1 MHz): 2.69
Dielectric loss tangent (according to JIS-C2138, 23° C.) (1 MHz): 0.0050
Nitrogen atom content: 1.01 wt. %

TABLE 10

|  |  | Example 29 | Example 30 | Example 31 | Example 32 | Example 33 | Example 34 | Example 35 | Example 36 | Comparative Example 6 |
|---|---|---|---|---|---|---|---|---|---|---|
| Composition | Curable compound | A | A | B | A | B | A | A | B | PEEK |
|  | Curable compound concentration (wt. %) | 10 | 10 | 10 | 10 | 10 | 10 | 10 | 10 | — |
|  | Solvent | Cyclohexanone | Cyclohexanone | Cyclohexanone | Cyclohexanone | Cyclohexanone | Cyclohexanone | Cyclohexanone | Cyclohexanone | — |
|  | Fiber | Carbon cloth | Glass cloth | Glass cloth | Carbon yarn | Carbon yarn | Glass yarn | Carbon fiber | Carbon fiber | — |

Example 37

Figure 16:
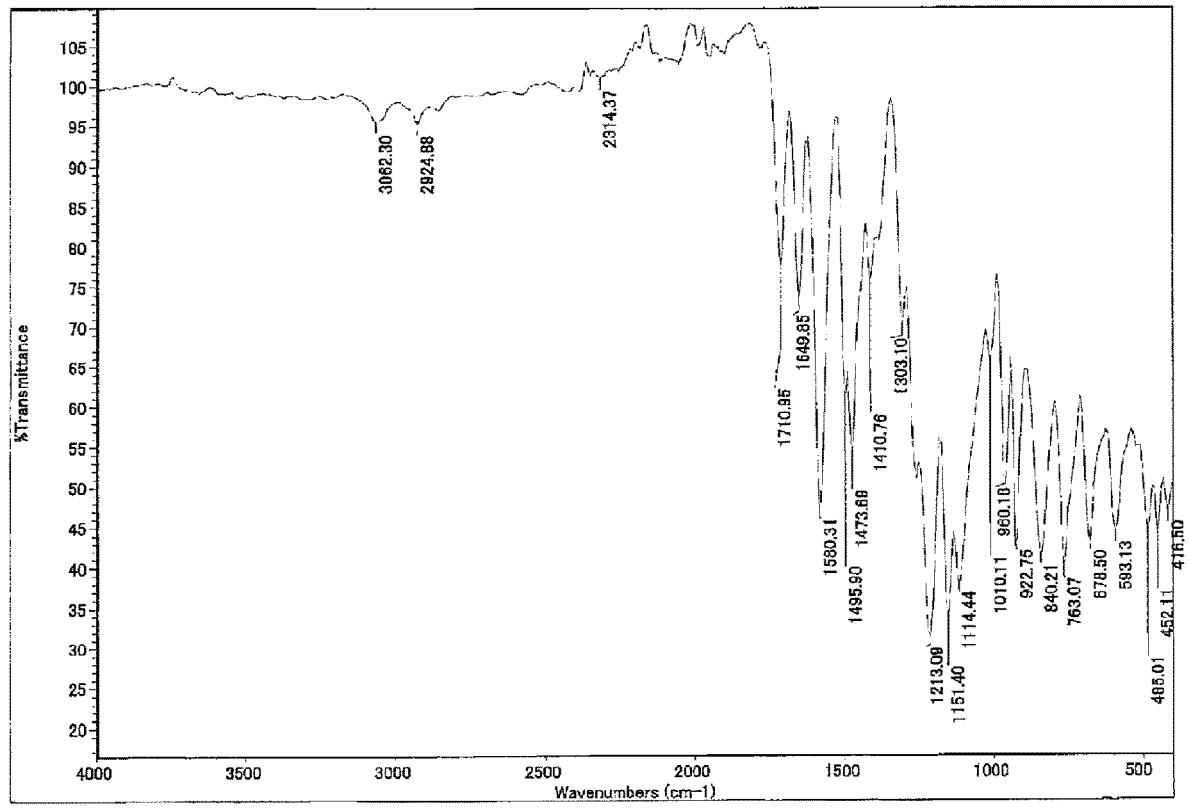
FIG. 16 is a figure showing an FTIR spectrum of a cured product of a curable compound A produced in Example.

The curable compound A was cured by a vacuum compression molding method, and a cured product was produced. Specifically, a mold in which the curable compound A had been charged was set in a press machine (30-ton manual hydraulic vacuum hot press, IMC-46E2-3 type, available from Imoto Machinery Co., Ltd.) and regulated at 50° C., and heated to 280° C. at 20° C./min in a vacuum and held at the temperature for 1 hour, and then the temperature was further increased to 320° C. at 20° C./min and maintained for 30 minutes. Thereafter, the press machine was air-cooled or water-cooled and when the temperature thereof became 100° C. or lower, the mold was taken out, and thus a cured product in a planer form (thickness: 0.2 cm) was produced. The FTIR spectrum of the produced cured product is shown in FIG. 16. The physical properties of the produced cured product were as follows.

Density (JIS K7112A 23° C.): 1.29 g/cm$^3$
Glass transition temperature (measured by DSC): 154° C.
Thermal expansion coefficient (according to JIS K 7197) (Tg or lower): 50.8 ppm/° C.
Thermal expansion coefficient (according to JIS K 7197) (Tg or higher): 263 ppm/° C.
Relative permittivity (according to ASTM D2520, 23° C.) (10 GHz): 2.94
Dielectric loss tangent (according to ASTM D2520, 23° C.) (10 GHz): 0.0056
Flame retardance (according to UL94V, thickness: 0.15 mm): V-1 grade
Nitrogen atom content: 1.30 wt. %

To summarize the above, configurations and variations according to an embodiment of the present invention will be described below.

[1] A curable compound comprising characteristics (a) to (e) below.
 (a) Number average molecular weight (calibrated with standard polystyrene): 1000 to 15000
 (b) Proportion of a structure derived from an aromatic ring in a total amount of the curable compound: 50 wt. % or greater
 (c) Solvent solubility at 25° C.: 1 g/100 g or greater
 (d) Glass transition temperature: 280° C. or lower
 (e) 5% weight loss temperature ($T_{d5}$) measured at a rate of temperature increase of 10° C./min (in nitrogen), for a cured product of the curable compound: 300° C. or higher

[2] The curable compound according to [1], where the curable compound is a compound represented by Formula (1).

[3] The curable compound according to [2], where $R^1$ and $R^2$ in Formula (1) are identical or different, and are each a curable functional group having a cyclic imide structure.

[4] The curable compound according to [2], where $R^1$ and $R^2$ in Formula (1) are identical or different, and are each a group selected from groups represented by Formulas (r-1) to (r-6).

[5] The curable compound according to any one of [2] to [4], where $D^1$ and $D^2$ in Formula (1) are identical or different, and are each a group selected from groups having structures represented by Formulas (d-1) to (d-4).

[6] The curable compound according to any one of [2] to [5], where $Ar^1$ to $Ar^3$ in Formula (I) and Formula (II) are identical or different, and are each a group in which two hydrogen atoms are removed from an aromatic ring structure having from 6 to 14 carbons, or a group in which two hydrogen atoms are removed from a structure in which two or more aromatic rings each having from 6 to 14 carbons are bonded through a single bond, a straight-chain or branched-chain alkylene group having from 1 to 5 carbons, or a group in which one or more hydrogen atoms of a straight-chain or branched-chain alkylene group having from 1 to 5 carbons are substituted with halogen atom(s).

[7] The curable compound according to any one of [2] to [6], where the structure represented by Formula (I) is a structure derived from benzophenone.

[8] The curable compound according to [7], where a proportion of a structural unit derived from benzophenone in a total amount of the compound represented by Formula (1) is 5 wt. % or greater.

[9] The curable compound according to any one of [2] to [8], where the structure represented by Formula (II) is a structure derived from at least one compound selected from the group consisting of hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A.

[10] The curable compound according to [9], where a proportion of a structural unit derived from hydroquinone, resorcinol, 2,6-naphthalenediol, 2,7-naphthalenediol, 4,4'-dihydroxybiphenyl, 4,4'-dihydroxydiphenyl ether, 4,4'-dihydroxybenzophenone, 4,4'-dihydroxydiphenyl sulfide, 4,4'-dihydroxydiphenyl sulfone, and bisphenol A in a total amount of the compound represented by Formula (1) is 5 wt. % or greater.

[11] The curable compound according to any one of [2] to [10], where L in Formula (1) is a group represented by Formula (L-1).

[12] The curable compound according to any one of [2] to [10], where L in Formula (1) is a group represented by Formula (L-1-1) or (L-1-2).

[13] The curable compound according to any one of [3] to [12], where a nitrogen atom content is from 2.8 to 0.1 wt. % relative to a total amount of the curable compound.

[14] The curable compound according to any one of [1] to [13], where a relative permittivity is 6 or less.

[15] The curable compound according to any one of [1] to [14], where a dielectric loss tangent is 0.05 or less.

[16] The curable compound according to any one of [1] to [15], where non-flammability of a cured product, having a thickness of 0.15 mm, of the curable compound measured by a method in accordance with UL94V is V-1 grade.

[17] A structural body in a particulate form or planer form, the structural body comprising a cured product or semi-cured product of the curable compound according to any one of [1] to [16].

[18] A laminate comprising a structure having a cured product or semi-cured product of the curable compound according to any one of [1] to [16] being laminated with a substrate.

[19] A method for producing a laminate, the method comprising placing the curable compound according to any one of [1] to [16] on a substrate and performing heat treatment to obtain a laminate having a structure having a cured product or semi-cured product of the curable compound being laminated with the substrate.

[20] The method for producing a laminate according to [19], the method comprising applying a molten material of the curable compound on a support formed from plastic and, after solidifying, obtaining a thin film containing the curable compound by releasing the produced thin film from the support.

[21] A composite material comprising a cured product or semi-cured product of the curable compound according to any one of [1] to [16] and a fiber.

[22] A solid material comprising a cured product of a curable compound, a 5% weight loss temperature ($T_{d5}$) measured at a rate of temperature increase of 10° C./min (in nitrogen) being 300° C. or higher, and a nitrogen atom content after being subjected to heat treatment at 320° C. for 30 minutes being from 2.8 to 0.1 wt. %.

[23] The solid material according to [22], where a peak is present in a region of 1620 to 1750 $cm^{-1}$ in an IR spectrum.

[24] The solid material according to [22] or [23], where the curable compound is a curable compound represented by Formula (1), and $R^1$ and $R^2$ in the formula are identical or different, and are each a curable functional group having a cyclic imide structure.

[25] The solid material according to [22] or [23], where the curable compound is a curable compound represented by Formula (1), and $R^1$ and $R^2$ in the formula are identical or different, and are each a group selected from groups represented by Formulas (r-1) to (r-6).

[26] An adhesive agent comprising the curable compound according to any one of [1] to [16].

[27] A paint comprising the curable compound according to any one of [1] to [16].

[28] A powder coating agent comprising the curable compound according to any one of [1] to [16].

[29] A sealing agent comprising the curable compound according to any one of [1] to [16].

[30] A method for producing a semiconductor device, a semiconductor device being produced by laminating a semiconductor substrate using the curable compound according to any one of [1] to [16] as an adhesive agent.

[31] A method for producing a semiconductor device, a semiconductor device being produced by sealing a semiconductor element using the curable compound according to any one of [1] to [16].

INDUSTRIAL APPLICABILITY

The curable compound according to an embodiment of the present invention has good solvent solubility. Furthermore, the curable compound has a low melting temperature and can be melted without using a device such as an autoclave. The curable compound is thus more rapidly cured by being subjected to heat treatment or irradiation. Therefore, the curable compound according to an embodiment of the present invention has good workability and can be suitably used as, for example, an adhesive agent, a sealing agent, and a paint.

The invention claimed is:
1. A curable compound having characteristics (a) to (e):
   (a) a number average molecular weight, calibrated with polystyrene standard, is from 1000 to 15000;
   (b) a proportion of a structure derived from an aromatic ring in a total amount of the curable compound is 50 wt. % or greater;
   (c) solvent solubility at 25° C. is 1 g/100 g or greater;
   (d) a glass transition temperature is 280° C. or lower; and

(e) a 5% weight loss temperature ($T_{d5}$) of a cured product of the curable compound, measured at a rate of temperature increase of 10° C./min, in nitrogen, is 300° C. or higher, wherein the curable compound is a compound represented by Formula (1):

(1)

where, $R^1$ and $R^2$ are identical or different, and each represent a group selected from groups represented by Formulas (r-1) to (r-6):

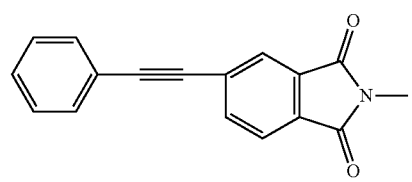
(r-1)

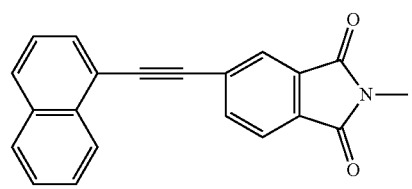
(r-2)

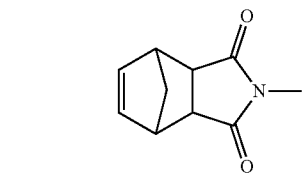
(r-3)

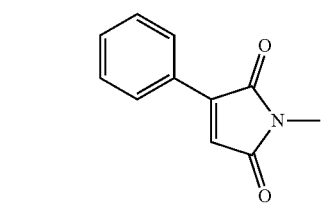
(r-4)

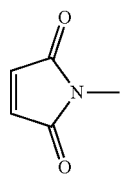
(r-5)

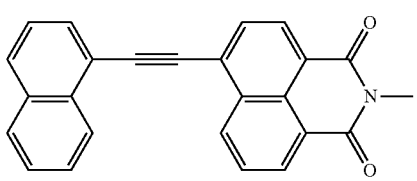
(r-6)

where, a bond from a nitrogen atom in each formula bonds to $D^1$ or $D^2$, $D^1$ and $D^2$ are identical or different, and each represent a single bond or a linking group selected from groups having structures represented by Formulas (d-1) to (d-4):

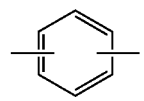
(d-1)

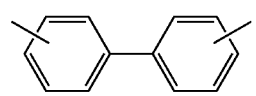
(d-2)

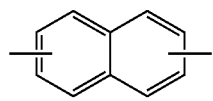
(d-3)

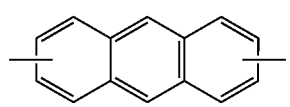
(d-4)

and L represents a divalent group represented by Formula (L-1-2):

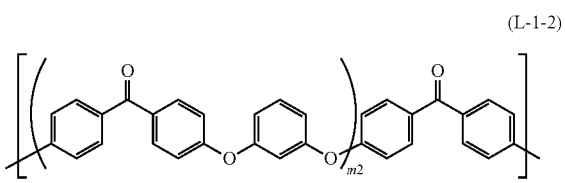
(L-1-2)

where, m2 represents a number from 2 to 50.

2. The curable compound according to claim 1, wherein a proportion of a structural unit derived from benzophenone in a total amount of the compound represented by Formula (1) is 5 wt. % or greater.

3. The curable compound according to claim 1 wherein a proportion of a structural unit derived from resorcinol in a total amount of the compound represented by Formula (1) is 5 wt. % or greater.

4. A structural body in a particulate form or planar form, the structural body comprising a cured product or semi-cured product of the curable compound described in claim 1.

5. A laminate having a configuration in which a cured product or semi-cured product of the curable compound described in claim 1 and a substrate are laminated.

6. A method for producing a laminate, the method comprising placing the curable compound described in claim 1 on a substrate and performing heat treatment to form a laminate having a configuration in which a cured product or semi-cured product of the curable compound and the substrate are laminated.

7. The method for producing a laminate according to claim 6, the method comprising coating a molten material of the curable compound on a support made of plastic, solidifying the coating, forming a thin film containing the curable compound, releasing the formed thin film from the support and laminating the formed thin film on a substrate, and performing heat treatment.

8. A composite material comprising a cured product or semi-cured product of the curable compound described in claim 1 and a fiber.

9. A solid material comprising a cured product of a curable compound,
wherein the curable compound is represented by Formula (1) below:

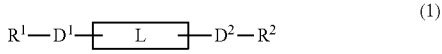
(1)

where, $R^1$ and $R^2$ are identical or different, and each represent a group selected from groups represented by Formulas (r-1) to (r-6):

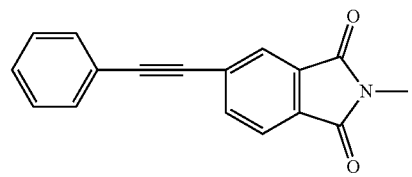
(r-1)

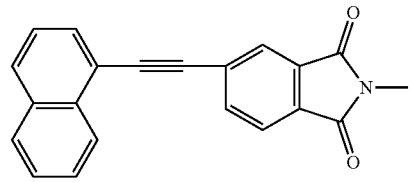
(r-2)

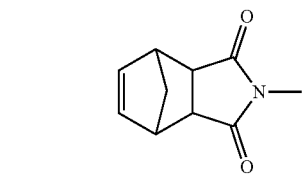
(r-3)

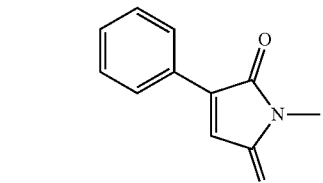
(r-4)

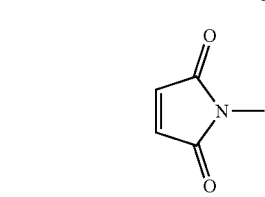
(r-5)

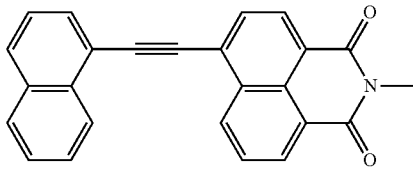
(r-6)

where, a bond from a nitrogen atom in each formula bonds to $D^1$ or $D^2$, $D^1$ and $D^2$ are identical or different, and each represent a single bond or a linking group selected from groups having structures represented by Formulas (d-1) to (d-4):

(d-1)

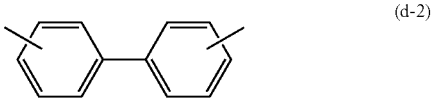
(d-2)

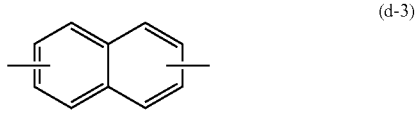
(d-3)

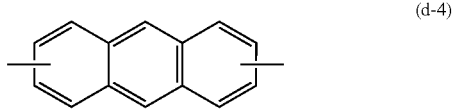
(d-4)

and L represents a divalent group represented by Formula (L-1-2):

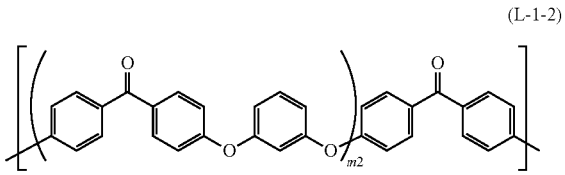
(L-1-2)

where, m2 represents a number from 2 to 50, wherein a 5% weight loss temperature ($T_{d5}$) measured at a rate of temperature increase of 10° C./min, in nitrogen, is 300° C. or higher, and a nitrogen atom content after being subjected to heat treatment at 320° C. for 30 minutes is from 2.8 to 0.1 wt. %.

10. The solid material according to claim 9, wherein a peak is present in a region from 1620 to 1750 cm$^{-1}$ in an IR spectrum.

11. A method for producing an adhesive agent, the method comprising dissolving the curable compound described in claim 1 in a solvent.

12. A method for producing a paint, the method comprising dissolving the curable compound described in claim 1 in a solvent.

13. A method for producing a sealing agent, the method comprising dissolving the curable compound described in claim 1 in a solvent.

* * * * *